United States Patent [19]

Seligson et al.

[11] 4,054,415
[45] Oct. 18, 1977

[54] BODY FLUID AND BLOOD ELECTROLYTE ANALYZER

[75] Inventors: David Seligson, Woodbridge; Stephen Clark Wardlaw, Branford; Philip C. Surh, Hamden, all of Conn.

[73] Assignee: Yale University, New Haven, Conn.

[21] Appl. No.: 626,060

[22] Filed: Oct. 28, 1975

[51] Int. Cl.$^2$ .................. G01N 1/14; G01N 1/16; G01N 1/18
[52] U.S. Cl. ................. 23/253 R; 23/259; 73/425.6
[58] Field of Search ............ 23/230 R, 253 R, 259; 235/151.35; 73/425.6

[56] References Cited

U.S. PATENT DOCUMENTS

| 3,728,080 | 4/1973 | Moran | 23/253 X |
| 3,764,268 | 10/1973 | Kosowsky et al. | 23/253 |
| 3,932,131 | 1/1976 | Rolfo-Fontana | 23/253 X |

*Primary Examiner*—R.E. Serwin
*Attorney, Agent, or Firm*—Silverman & Cass, Ltd.

[57] ABSTRACT

An apparatus for testing body fluid or blood electrolytes in a body fluid or blood serum sample includes three testing stations. The blood sample is automatically transported from an input point serially and in a linear manner along a track past the three testing stations to an output point. The first testing station removes a first portion of the sample at a first location along the track and has a rotating structure including a container which receives and stores the first portion and rotates it to a first testing position at a first time. A testing structure tests the first portion while at the first testing position at that first time.

The second testing station removes a second portion of the sample at a second location along the track and includes a second rotating structure including a container which receives and stores the second portion and rotates the stored second portion to a second testing position, also at the first time. A second testing structure tests the second portion while at the second position at the first time.

A third testing station removes a third portion of the sample at a third location along the track and tests the removed third portion at the noted first time so that all the tests are performed simultaneously and the results thereof can be derived simultaneously without the need for memory, delay or control apparatus.

68 Claims, 8 Drawing Figures

BODY FLUID AND BLOOD ELECTROLYTE ANALYZER

BACKGROUND OF THE INVENTION

This invention relates to automated body fluid or blood analysis equipment and more particularly to automated body fluid or blood electrolyte analysis equipment.

The analysis of a number of factors in blood and blood serum in order to obtain a more thorough and complete picture of a person's physical condition has become a standard medical procedure today. Ranking high among the blood constituents analyzed in order to determine general health are the so-called blood electrolytes. Blood electrolytes are extra-cellular ions contained in the blood, the four major extra-cellular ions being sodium, potassium, chloride and bicarbonate. These four are generally measured as a group because of their interrelationship. The measurement results can provide information necessary in order to maintain a proper chemical balance for a patient during intravenous feeding, and in order to ascertain the general health or specific physical problem of a patient because each measurement either provides an indication of specific physical activity or response, or assists in understanding overall physical condition.

Concentration of sodium ions in the blood is one indication of osmotic pressure. If a person's sodium chloride content increases as indicated by an increase of sodium ions, dehydration has occurred.

Concentration of potassium ions is an indicator of cardiac muscle activity. If the potassium concentration is high above the normal limit, this indicates a weak cardiac muscle which can stop at any time. A low potassium concentration indicates excessive cardiac muscle activity which can result in heart fibrillation.

Human blood has an acid base content that must be maintained within predetermined limits in order to support life. An acid alkaline measure of blood is normally defined in terms of pH. The bicarbonate concentration is a good incicator of the blood pH or blood acid-alkaline balance.

Chloride is not a special indicator in and of itself. However, it is necessary in order to obtain a complete electrolyte picture.

The normal ranges of the electrolyte concentrations are:

sodium: 135-148 Meq
potassium: 3.5 -5.3 Meq
chloride: 98 -108 Meq
bicarbonate: 23 -30 Meq Sodium and potassium are positive ions, while chloride and bicarbonate are negative ions. If typical values were selected for each of the four and the positive ion values and negative ion values summed and then subtracted from one another there would be a difference of 16 ±2. This difference is known as the "anion deficit" or "anion gap".

As noted above there is a range of acceptable concentration values for each of the electrolytes. When an electrolyte analysis is performed all four noted electrolytes are measured and the anion gap is calculated. If it is substantially different from the 16±2 noted above and if the electrolyte concentrations are all within or near normal range, a clear indication is provided that there is some problem associated with a particular patient whose blood is analyzed. On the other hand if one concentration value is clearly outside the normal range, all others are within range and the anion gap differs from normal by the variation in the one concentration, all indicators point to the same problem.

Automated systems in use today which measure all four noted electrolyte concentrations have errors of the order of 2 to 3 Meq. in all but the potassium analysis. The resultant total error when all values are added together can be as great as ±8 Meq. The magnitude of this error is so great that it seriously detracts from the usefulness of a blood electrolyte analysis, particularly in emergency situations where the analysis must be performed stat.

A number of different tests and test methods may be employed for the determination of each one of the four primary electrolyte concentrations. The nature of the test will determine the accuracy of the result, that is, how close the result is to the correct answer. The specific apparatus used to perform the test will determine the precision or repetitive consistency of the test results. Generally, sodium and potssium can be determined simultaneously and in one test by use of a flame photometer. Current day photometers employ a known concentration of lithium as a reference in order to ascertain sodium and potassium concentrations. Bicarbonate and chloride concentrations are determined most accurately by a titration method. However, titration methods and apparatus heretofore available for performing titrations do not provide precise results when employed in an automatic apparatus.

The flame photometry procedure and titration procedures available take different periods of time so that if they are employed in an automated testing apparatus, the various tests must be synchronized and the results of each stored and then made available after the completion of the last test. This procedure is cumbersome and time consuming, and may require a memory for storage of the test results from the various tests until the entire testing procedure has been completed. It is desirable to reduce the complexities of such structures and eliminate any memory storage of test results. It is also desirable to perform the tests as quickly as possible in order to satisfy emergency conditions, and to provide the results simultaneously in order to allow immediate calculation of the anion gap and analysis of the patient's blood.

SUMMARY OF THE INVENTION

In practicing this invention, an apparatus is provided for testing the electrolyte concentrations in a blood serum sample and other body fluids. The apparatus includes a structure for moving a plurality of blood samples serially and in a linear manner along a track from an input to an output. Three testing stations are provided along the track. The first testing station removes a first portion of the sample at a first location along the track and stores the first portion in a rotating structure which rotates to a first testing position in a first predetermined time. A first testing structure tests the first portion while at the first testing position.

A second testing station removes a second portion of the sample at a second, further location along the track and stores the second portion in a rotating structure which rotates the second portion to a second testing position at the same first predetermined time. A second testing structure tests the second portion while at this second testing position.

A third testing station removes a third portion of the sample at a third location further along the track. A third testing structure receives this third portion and tests same at the first predetermined time so that all three tests are performed simultaneously. Output devices are provided for simultaneously displaying the test results.

The first testing station is a flame photometer which has a burner tube and chimney and structure positioned between the burner tube and chimney for producing a laminar flow of air through the chimney and along the burner.

The second testing station includes a photometric analysis apparatus which employs two dyes of known concentration, one of which is light absorbent at a first frequency which is invariant with changes in a chemical process and the other has an absorbence at a second light wavelength which varies in accordance with the chemical process. The dye is added to the sample to be analyzed and light at the two noted wavelengths is alternately passed through the dyed sample along the same path. At this time the chemical process is started within the sample. Comparison of the ratio of the light intensities transmitted through the dye samples is used to determine the end point of the chemical process.

The third station includes a titration device which causes the sample to flow in a circular path during the titration process for thoroughly mixing the sample to ensure uniform titration. Structure is present in the circular path taken by the sample which acts to disturb the circular flow further enhancing uniform titration of the sample.

DETAILED DESCRIPTION OF THE PREFERRED EMBODIMENT

Figure 1:
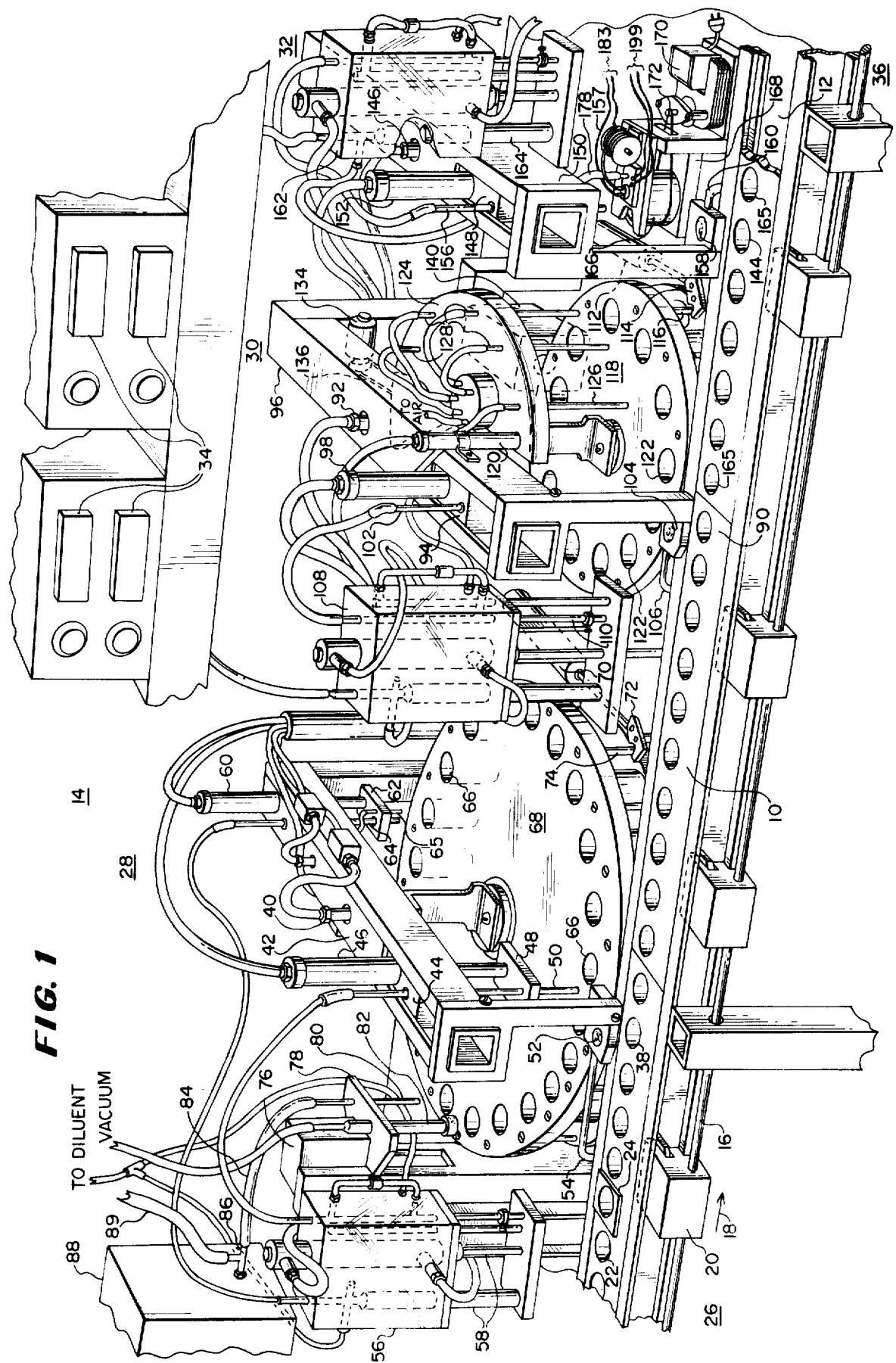
FIG. 1 is a perspective view of the blood electrolyte testing apparatus of this invention showing all three stations and the visual display devices.

Referring to FIG. 1, a number of elongate plastic plates 10 are shown seated on a linear elongate track 12 in the blood electrolyte apparatus 14. A control suystem operates a hydraulic actuator (not shown) which actuates rod 16 to move or step in the direction noted by arrow 18 and then return to its original position at regular timed intervals. Actuator device 20, secured to rod 16, has fingers connected with a one-way clutch mechanism (not shown) which bear against the side edge of plastic plates 10. These fingers move plastic plates 10 forward in the direction indicated by arrow 18, in a stepwise fashion, when rod 16 and actuator device 20 are operated. When rod 16 and actuator device 20 return to their original position the one-way clutch mechanism in actuator device 20 releases the fingers allowing actuator device 20 to return without a corresponding movement for plastic plates 10.

Plastic plates 10 have a number of holes 22 formed therein which pass through the plates from the top surface to the bottom surface. A plastic sample holder 24 seats on the top surface of a plate 10 and includes a portion which inserts into one of holes 22. The blood serum from a patient's blood, which has been spun down to separate the blood serum from the red cells, is discharged into each plastic sample holder 24, for example by a technician employing a pipette, and the sample holder 24 is appropriately identified with a patent identifier. The sample is fed into plastic holder 24 at an input area identified generally by the number 26.

Each sample travels along track 10 in a linear stepwise fashion past three testing stations identified generally by the numbers 28, 30 and 32. At testing station 28, the first station passed by a sample a test is performed for two blood serum electrolyte constituents, namely, sodium (Na+) and potassium (K+). At testing station 30, the second station passed by a sample, each blood sample is tested for a single blood electrolyte constituent, namely bicarbonate (HCO$_{-3}$). At testing station 32, the third station passed by a sample, each sample is tested for a single blood electrolyte constituent, namely, chloride (Cl-).

Each blood serum sample being tested moves stepwise along track 12 past each of the three testing stations. When a sample passes testing station 32 the structures at the testing stations, 28, 30 and 32 will simultaneously test the portions of the same blood serum sample which have been drawn from a holder 24 as it passed the three stations, and the test results will be simultaneously displayed by the four readout devices shown at 34. After a plastic plate 10 and sample holder 24 have passed testing station 32 and the tests of the blood serum sample contained therein have been completed, it will enter an output area of track 12 identified by the number 36 where sample holders 24 and the samples therein may be removed and discarded. Plates 10, after removal from track 12, may be reseated onto track 12 at input area 26.

Following a first blood serum sample along through the electrolyte analyzer 14, the sample is added to a holder 24 by a technician at input area 26 and moves stepwise along track 12 to a first location 38 in front of first testing station 28. When the first sample has stepped to location 38 and a previously drawn sample is dispensed hydraulic piston 40, mounted in a support bar 42, is actuated by the control system causing a carrier 44 slidably mounted in support bar 42, to move forward towards track 12. A hydraulic piston 46 is mounted in carrier 44 and supports another carrier 48 in which is vertically mounted a pipette 50. When piston 40 has moved carrier 44 to the outermost position, piston 46 is actuated moving carrier 48 downward so that pipette 50 passes through a sponge 52 and into holder 24. The sponge removes any blood serum which may have attached to the outer walls of pipette 50 from a previous sampling, and vacuum line 54 attached to sponge 52 removes the blood serum drawn into sponge 52.

After pipette 50 has moved to its downwardly extended position and is inserted into holder 24, a diluter pump 56 is actuated by the hydraulic piston therein to move the pistons therein, shown generally by the number 58, downward out of their cylinders. This causes a vacuum that acts to draw a predetermined first portion of sample from sample holder 24 into pipette 50. The remaining cylinders in diluter pump 56 draw in a diluent from a diluent reservoir. Pistons 58 reach their outermost or extended position and the operation of diluter pump 56 is interrupted. Hydraulic piston 46 is again actuated to move carrier 48 and pipette 50 upwards out of holder 24 to a retracted position. As the pipette passes through sponge 52, the outer surface again is wiped to remove excess and the excess absorbed into sponge 52 is drawn off by way of vacuum line 54.

When carrier 48 reaches its uppermost position hydraulic piston 46 is stopped and hydraulic piston 40 is actuated moving carrier 44 from its outermost position over track 12 to its innermost position where it stops.

Simultaneously with the dispensing of a previously drawn sample and while the previously described operation of pistons 40 and 46 occurs, a hydraulic piston 76 supporting a carrier plate 78 actuates to move the carrier plate downward. Carrier plate 78 carries two pipettes 80 and 82 which extend into adjacent cylindrical containers 66 formed in a rotatable carousel structure 68 as carrier plate 78 moves downward to its lowermost position. There are 24 cylindrical containers formed in carousel 68, pipette 80 descending into the container at the nineteenth location and pipette 82 descending into the container at the twentieth location.

Pipette 80 is connected by way of tubing 84 to the carburetor 86 of a flame photometer 88. Air for the carburetor 86 of flame photometer 88 is supplied by way of tubing 89. The air creates a vacuum pressure within carburetor 86 that acts to aspirate a portion of the diluted sample from container 66 into and through pipette 80 and through carburetor 86. When the sample is aspirated, it is passed into the flame portion of flame photometer 88. The flame intensity of the burning sample is analyzed to determine the concentration of sodium and potassium.

At the same time as the sample is being aspirated from container 66 by pipette 80, the mixture remaining in the container 66 at location 20 which is the mixture that remains after the preceding test is performed, is aspirated by pipette 82. A sponge attached to the end of pipette 82 acts to clean the sidewalls of the container as the pipette is withdrawn.

When all of the sample has been aspirated from container 66 at location 20 and when the test performed by flame photometer 88 is complete, both being performed in a predetermined time period, the control system operates hydraulic piston 76 to raise carrier plate 78 to its upper position thus removing pipettes 80 and 82 from the containers in carousel 68.

Upon full withdrawal of pipettes 80 and 82 and return to their uppermost positions, and while carrier 44 is in its innermost position, the control system for the apparatus actuates a hydraulic piston 70 positioned adjacent to rotatable carousel structure 68. Piston 70 has a ratchet mechanism 72 attached thereto which grips one of a number of posts 74 passing through the rotatable carousel structure 68. There are 24 posts on carousel structure 68 so that the number of posts and number of cylindrical containers 66 are equal. Actuation of piston 70 causes ratchet mechanism 72 to draw backwards towards piston 70. This movement causes rotatable carousel structure 68 to rotate or index one step in the counterclockwise direction. This one step rotation moves a new cylindrical container 66 into position under pipettes 50, 80 and 82. Piston 70 now is operated in reverse fashion by the control system so that ratchet mechanism 72 moves forward ratcheting to and gripping another post 74.

Simultaneously with the operation of piston 70 and ratchet mechanism 72 and the one step counterclockwise rotation of carousel structure 68, rod 16 again actuates causing actuator device 20 to move each plate 10 and holder 24 one step in their stepwise linear progression along track 12 in order to position a new blood sample at first location 38 along track 12.

After carousel 68 and track 12 are stepped, hydraulic piston 46 and a hydraulic piston 60 are actuated. Hydraulic piston 60 also is mounted in support bar 42 and supports a carrier 62 in which are mounted pipettes 64 and 65. Actuation of hydraulic pistons 46 and 60 causes carriers 48 and 62 to move downward towards cylindrical containers 66. The cylindrical container 66 into which pipette 50 descends is the container at the first location and the cylindrical container into which pipettes 64 and 65 descend is the container at the thirteenth location on carousel 68.

Pipettes 64, 65 and 50 reach their lowermost position in cylindrical containers 66 and diluter pump 56 again actuates by operation of the hydraulic piston therein moving pistons 58 upward. The upward movement causes the sample contained in pipette 50 to be discharged into the container 66 at the first location along with a predetermined amount of the desired diluent. Diluents will also be discharged by way of pipette 64 into container 66 at the thirteenth location in order to dilute the sample therein to the desired dilution ratio. Pipette 65 bubbles air through the mixture in container 66 to effect uniform mixing.

Pistons 58 continue moving upward in diluent pump 56 until they reach their uppermost position at which time they stop. At this time, all of the blood serum in pipette 50 and the desired diluent has been discharged into containers 66 at the first and thirteenth locations. Next, hydraulic pistons 46 and 60 are again actuated causing carriers 48 and 62 to move upwards withdrawing pipettes 50, 64 and 65 from containers 66 at the first and thirteenth locations on carousel 68 and terminating the operating cycle.

The sample previously noted as being located at first location 38 continues to be moved stepwise along the track 12. When it is stepped for the twelfth time after being in first location 38 it moves into a second location 90 in front of second testing station 30. Once the first sample is positioned at second location 90 and a previously drawn sample is dispensed, a first hydraulic piston 92 is actuated causing a carrier 94, slidably seated in support bar 96 to move forward towards track 12. Piston 92 extends carrier 94 to its outermost position and then a hydraulic piston 98, mounted in carrier 94 and carrying a carrier 100 (not shown) is actuated by the control system to move carrier 100 downwards. Carrier 100 is substantially identical to carrier 48. Pipette 102, mounted in carrier 100, moves downward with the carrier passing through a sponge 104 to which is attached a vaccum line 106 and extending into sample holder 24. After piston 98 extends carrier 100 to its lowermost position, it stops and diluter pump 108 is actuated by way of the hydraulic piston therein to move the pistons therein and identified by the number 110 downward out of the cylinders in diluter pump 108. This downward motion creates a vacuum within the cylinders of pump 108. One cylinder is coupled to pipette 102 and causes a predetermined quantity of the blood serum in the first sample at location 90 to be drawn into pipette 102. Another cylinder is connected to a reagent reservoir and will be filled with the reagent therein. The first cylinder also is connected to a reagent reservoir and will be partially filled with reagent, only a small volume of blood serum being drawn into pipette 102.

Pistons 110 reach their outermost position and the operation of diluter pump 108 stops. Thereafter, hydraulic piston 98 is actuated to raise carrier 100 and pipette 102 out of sample holder 24 to a retracted position. As pipette 102 passes through sponge 104 the outer surface is wiped to remove serum thereon and the serum absorbed into sponge 104 is drawn off by vacuum line 106.

Carrier 100 reaches its uppermost position and the control system terminates operation of hydraulic piston 98 and actuates hydraulic piston 92. Hydraulic piston 92 now moves carrier 94 inward to its retracted position. Upon reaching its maximum inward position, hydraulic piston 92 is deactivated.

Substantially simultaneously with the return of piston 92 to its retracted position, hydraulic piston 120, secured to support bar 96, operates to raise a semicircular plastic plate structure 124 towards carousel 118 thus completing a previous testing cycle. When plate structure 124 reaches its uppermost position, hydraulic piston 120 is deactuated.

After deactuation of pistons 92 and 120, a hydraulic piston 112 is actuated drawing a ratchet mechanism 114 rearwardly. Piston 112 and ratchet 114 are identical to piston 70 and ratchet 72. Piston 112 and ratchet 114 are positioned adjacent a rotatable carousel 118 with ratchet 114 gripping one of a number of posts 116 passing through the rotatable carousel structure 118. There are 12 posts on carousel 118, the number of posts being equal to the number of cylindrical containers 122 formed in carousel 118. Actuation of piston 112 causes ratchet mechanism 114 to draw backwards towards piston 112 causing rotatable carousel structure 118 to rotate or index one step in the counterclockwise direction. This one step rotation moves another cylinder 122 into position under pipette 102. Piston 112 now is operated in a reverse fashion by the control system so that ratchet mechanism 114 moves forward to its original position ratcheting to and gripping another post. A one way slip clutch in ratchet mechanism 114 will prevent it from rotating carousel 118 in a clockwise direction as it moves forward.

As explained with regard to station 28, plates 10 are moved in stepwise fashion along track 12 by the movement of rod 16 and actuator device 20 simultaneously with the movement of piston 112 in order to position a new blood serum sample at second location 90 along track 12.

Next, hydraulic piston 98 and hydraulic piston 120 again are actuated. Actuation of piston 98 causes carriage 100 to move downward so that pipette 102 will be lowered into the cylindrical container 122 formed at the first location in rotatable carousel 118. As already noted, there are 12 cylindrical containers formed in carousel 118 as compared to the 24 cylindrical containers identified in carousel 68.

Figure 2:
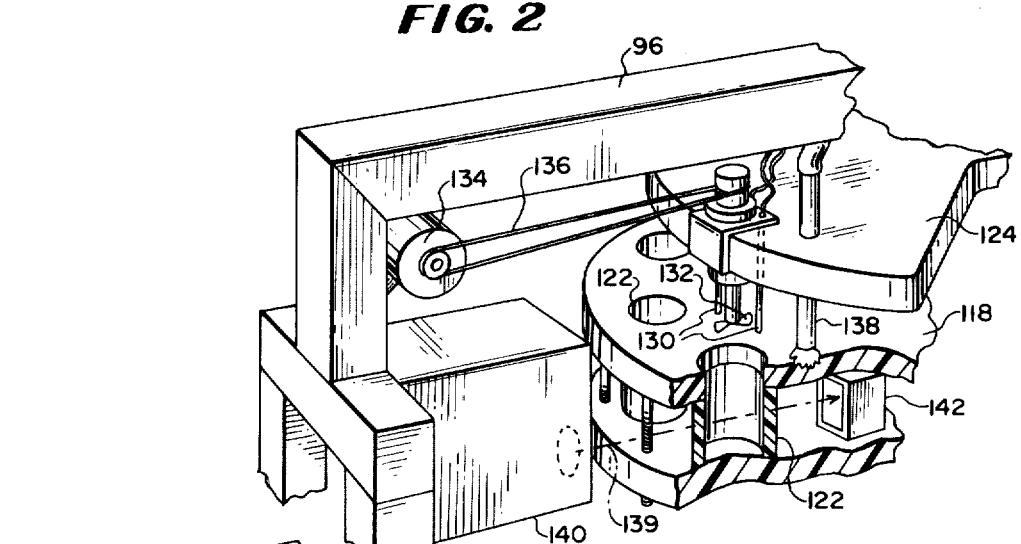
FIG. 2 is a perspective view detailing a portion of the second testing station shown in FIG. 1.

Plastic plate structure 124 carries a first pipette, identified by the reference number 126 and four additional pipettes identified by the reference number 128. A pair of copper electrodes shown more clearly in FIG. 2 and identified by the number 130 also is secured to plate structure 124 with a propeller 132 rotatably secured to structure 124, and positioned between the electrodes 130. Propeller 132 is connected to a motor 134 by way of a drive belt 136. A syphon pipette 138 also is secured to plate 124.

Plate 124 moves down to its lowermost position with the downward movement of carrier 100. When plate 124 reaches its lowermost position, pipettes 126, 128 and 138, copper electrodes 130 and propeller 132 each are inserted into a cylindrical container 122 in carousel structure 118. Pipette 126 is inserted into the container at the second location, pipettes 128 are inserted into containers at the third, fourth, fifth and sixth locations, copper electrodes 130 and propeller 132 are inserted into the container at the seventh location and pipette 138 is inserted into the container at the eighth location.

Diluter pump 108 now is actuated by the hydraulic piston therein causing piston 110 to move upwards into the cylinders forcing the diluent from the cylinders. Part of the diluent will pass from the first cylinder to pipette 102 forcing out the second portion of the first blood serum, sample drawn into pipette 102 and a predetermined quantity of diluent. This is injected into the cylindrical container 122 at the first location on carousel 118, opposite to the second location 90. A second diluent, which in this case is actually a mixture of dyes of specific concentration, is passed from another cylinder in pump 108 through pipette 126 into the cylindrical container 122 at the second location on carousel 118.

Simultaneously, air is passed to and through pipettes 128 extending into the mixture in the cylindrical containers 122 at carousel locations three, four, five and six. The air is passed through the solution as a part of the chemical process in order to cause a disassociation of carbon dioxide from the chemical solution in the containers and in order to remove the carbon dioxide from the mixture in each container.

At the same time a photometric analysis apparatus, which tests the sample at station 30, operates and produces a light beam shown by a dotted line 139, which is passed from a light source 140 to and through the container 122 in which electrodes 130 and propeller 132 are present to a photodetector 142. The light path is below the electrodes and propeller so as to be unobstructed. The bicarbonate concentration determination employs a titration process wherein current is coupled to electrodes 130 in order to produce the titration. Motor 134 operates to rotate drive belt 136, rotating propeller 132 during the titration in order to ensure uniform mixing of the liquid in cylinder 122 during the titration process.

Again at the same time pipette 138 is inserted in the container 122 at the eighth location of carousel 118 and is connected to a source of vacuum or to a peristaltic pump for drawing off the liquid suspension contained in this particular container, which is the mixture remaining after the concentration measurement at location seven.

When pistons 110 reach their uppermost positions diluter pump 108 is deactuated and hydraulic piston 98 again is actuated moving carrier 100 and pipette 102 out of the container 122 at the first location of carousel 118. Thereafter, the portion of the operating cycle previously described for moving pipette 102 to and drawing in sample from holder 24, is repeated for the next sample.

At the end of a predetermined time period, the time period being sufficient to completely perform the titration process, obtain another sample, prime pump 108 with diluent, remove the carbon dioxide from the samples in the containers and remove the sample itself from the container at location seven and after piston 92 has drawn carrier 94 to its innermost position, piston 120 again is actuated moving plate 124 upward so that the apparatus mounted to plate 124 is withdrawn from carousel 118. When the plate 124 has risen to its uppermost position, the control system terminates further operation of piston 120 and an operating cycle is completed.

Retracing somewhat generally the operation to this point, the first blood serum sample in a holder 24 reaches the first location 38 in front of the first testing station 28 and the first portion of the blood sample is withdrawn from the holder 24. After the first portion is withdrawn, a test is performed at all three stations 28, 30 and 32. After the test carousel 68 and the plate 10 holding the holder 24 containing the first sample are indexed once so that carousel 68 moves one step in a counterclockwise direction and plate 10 moves one step in the linear direction along the track 12. Then the first portion of the first sample withdrawn from holder 24 is deposited into cylindrical container 66 opposite to the first location 38. At this time the holder 24 containing the first sample has already indexed one position along the linear track as previously noted.

The first sample in the holder 24 indexes a total of twelve times and after the twelvth index it is in the second location 90 along track 12 and in front of carousel 118. The second portion of the sample is withdrawn from holder 24 at this location. While the second portion is withdrawn, a test is performed at all three stations 28, 30 and 32. After the test carousel 118 the plate 10 on track 12 holding the holder 24 containing the first sample is indexed once so that the carousel 118 moves one step in a counterclockwise direction and plate 10 moves one step in the linear direction along the track 12. Then the second portion of the first sample withdrawn from holder 24 is deposited into the container 122 opposite the second location 90.

The first sample being followed along track 12 indexes six times along the track 12 after second location 90. After the sixth index, the holder 24 will be at a third location 144 along the track. When the sample is at this third location, the first portion will have indexed around carousel 68 17 times, thus being located at the eighteenth location; and the second portion of the first sample will have indexed around carousel 118 five times, being located at the sixth position of carousel 118.

When the first sample has stepped to location 144, hydraulic piston 146 is actuated by the control system causing a carrier 148 slidably seated in a support bar 150 and attached to hydraulic piston 146 to move forward along the support bar towards track 12 and sample holder 24. Carrier 148 reaches its furthermost forward position and the control system stops further movement of piston 146 and actuates a hydraulic piston 152 mounted in carrier 148. Hydraulic piston 152 supports a carrier 154 (not shown), which is identical to carrier 48, and in which is secured a pipette 156. Actuation of hydraulic piston 152 causes carrier 154 and pipette 156 to be moved downward towards the holder 24 in track 12. As pipette 156 is lowered towards holder 24, it passes through a sponge 158 which removes excess sample adhering to the outside surface of the pipette. Vacuum line 160 draws the excess from sponge 158. After pipette 156 reaches its lowermost position and is inserted into the holder 24 containing the first sample, hydraulic piston 152 is deactuated.

Upon deactuation of hydraulic piston 152, a diluter pump 162 is actuated by way of a hydraulic piston therein, causing pistons 164 in pump 162 to move downwards withdrawing from the cylinders in pump 162. As the pump pistons withdraw from the cylinders, they will create a vacuum. One of the cylinders is coupled to pipette 156 and will cause a predetermined amount of the firt sample, referred to as the third portion of the first sample, to be drawn into pipette 156. At the same time, a predetermined quantity of diluent will also be drawn into the one cylinder and a predetermined quantity will be drawn into another one of the cylinders. A third cylinder, connected to the testing apparatus at the third testing station 32, at this time will create a vacuum and when titration of the preceding sample is complete will draw a predetermined amount of waste fluid from the testing station into the cylinder. When pistons 164 reach their lowermost point fully withdrawn from the cylinder, the diluter pump operation is interrupted.

When diluter pump 162 is interrupted, hydraulic piston 152 again actuates moving carrier 154 and pipette 156 upward out of holder 24 and the first sample. As it rises, the excess first sample clinging to the outer surface of pipette 156 is removed by passage through sponge 158 and is drawn off through vacuum line 160.

Carrier 154 and pipette 156 reach their uppermost position and hydraulic piston 152 stops. Thereafter piston 146 actuates moving carrier 148 rearward along support bar 150 to its innermost position. When carrier 148 reaches its innermost position, hydraulic piston 146 is deactuated.

Upon deactuation of hydraulic piston 146, the control system actuates the hydraulic piston attached to rod 16 causing a stepwise movement of rod 16 and actuator device 20 in the direction shown by arrow 18. This results in a stepwise movement of plate 10 and holder 24 moving the first sample to the next position and moving a new sample into the third location 144. It is to be understood, of course, that this stepwise movement only occurs after deactuation of piston 146 and after a period of time sufficient to perform the tests at stations 28, 30 and 32; the movement of the hydraulic pistons for withdrawing the first, second and third of the first sample portions being performed simultaneously with the performance of tests at stations 28, 30 and 32.

With the last noted indexing, the first sample heretofore described is in what is termed the read position 165 and the first and second portions at testing stations 28 and 30 respectively are located at the first and second testing positions, location nineteen on carousel 68 and location seven on carousel 118 respectively, where they may be tested by the appropriate testing apparatus.

Next the control system actuates hydraulic piston 152 which causes carrier 154 and pipette 156 to move downward to the testing apparatus 157 located at testing station 32. Hydraulic piston 152 is stopped when carrier 154 and pipette 156 reach the lowermost position and diluter pump 162 is actuated causing pistons 154 to rise and dispel the fluid within the cylinders in pump 162. This causes the third portion of the first sample in pipette 156 to be discharged into the testing apparatus 157 at testing station 32 along with a predetermined quantity of the desired waste fluid. The excess diluent from a preceding test, which has been stored in one of the cylinders in diluter pump 162, is discharged to waste.

The hydraulic system terminates further operation of diluter pump 162 when pistons 164 reach their uppermost position and the testing operation performed at station 32 is initiated. Simultaneously, hydraulic piston 152 again is actuated, moving carrier 154 and pipette 156 upward out of apparatus 157. Thereafter the portion of the operating cycle previously described for moving pipette 156 to and drawing a sample portion from holder 24 is repeated for the next sample.

Figure 5:
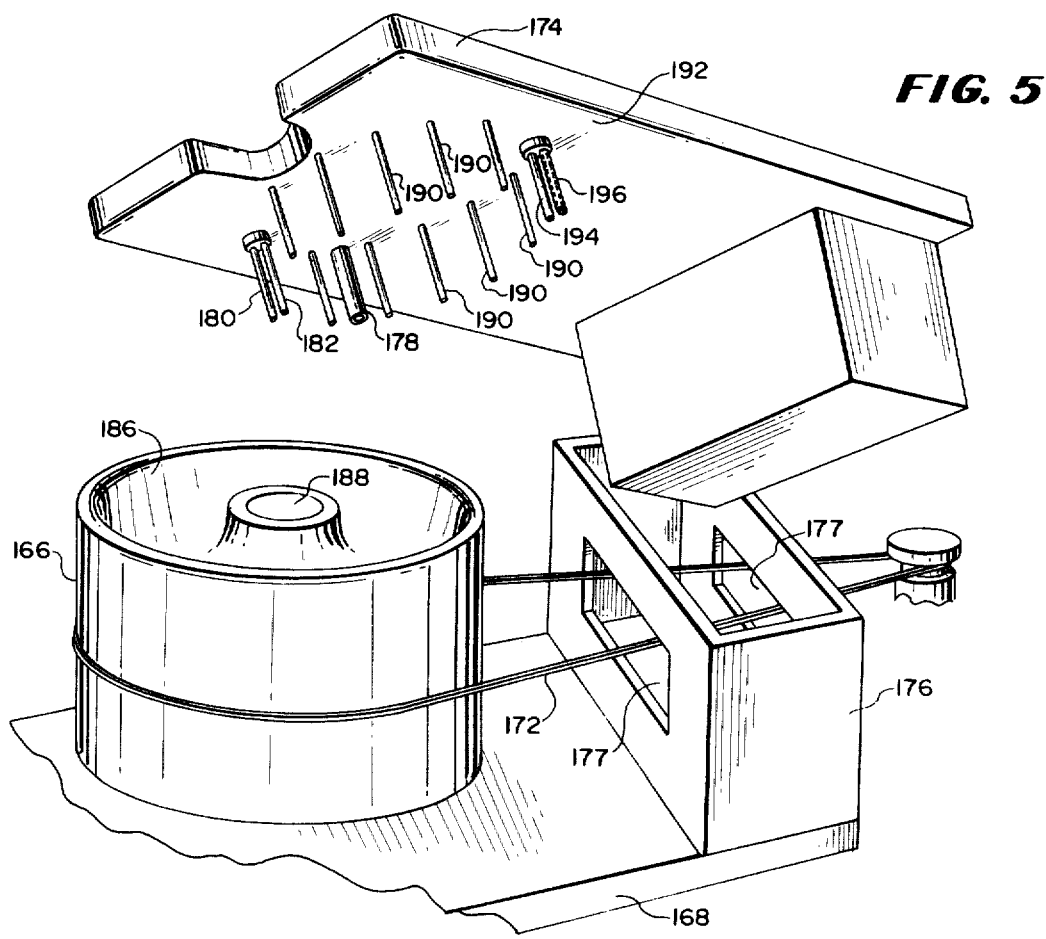
FIG. 5 is an exploded perspective view of a portion of the structure located at the third station in FIG. 1.

At station 32 a coulometric titration process is performed for determining the chloride concentration is a blood serum sample. Referring to FIGS. 1 and 5, the testing apparatus at station 32 includes a circular housing 166 rotatably mounted on a base structure 168. A motor 170 is secured to base 168 and is connected to circular housing 166 by way of a drive belt 172. A cover 174 mates with an upstanding support member 176 covering the top of housing 166. Drive belt 176 extends from motor 170 to housing 166 through slots 177 formed in upstanding support member 176.

The syphon drain line 178 previously noted as connected between the testing apparatus 157 and diluter pump 162 passes through cover 174 to the interior of housing 166 in order to provide the syphoning of waste fluid as previously explained. A pair of silver electrodes 180 and 182 is shown mounted on cover 174 and is connected to a titration circuit, to be described subsequently by conductor 183. Electrode 180 is fixedly mounted to and extends through the cover to the interior of housing 166 and electrode 182 extends through an aperture in cover 174 and is in frictional engagement therewith so that electrode 182 may be drawn through the cover 174. Electrode 182 is the end portion of a spool of silver wire shown by the reference number 184.

Housing 166 has an annular trough 186 formed therein by the outer walls of housing 166 and a center island 188. A bottom view of housing cover 174 in FIG. 5, shows the silver electrodes 180 and 182 which are disposed within trough 186 and the mixture of the first sample third portion and diluent therein when cover 174 is properly noted with support member 176.

A number of polytetrafluoroethylene rods 190 are shown secured to the inner surface 192 of cover 174 ane extend axially perpendicular to the inner surface. The rods form a circle with electrodes 180 and 182 being included in the circle. Rods 190 extend into the annular trough 186 and the mixture of first sample third portion and diluent therein when cover 174 is mated with support member 176.

A second pair of electrodes 194 and 196 is mounted in cover 174 and also is connected to the titration circuit by way of conductors 197 in the same manner as electrodes 180 and 182. Electrodes 194 and 196 are mounted in the same circle formed by electrodes 180 and 182 and rods 190 and are substantially diametrically opposite to electrodes 180 and 182 on the formed circle. Electrodes 194 and 196 also extend into the annular trough 186 and the mixture of the first sample third portion and diluent therein when cover 174 is mated with support member 176. The axis of electrodes 194 and 196 are positioned in a plane extending radially from the center of housing 166 and the axis of electrodes 180 and 182 are positioned in a plane extending perpendicular to a radius of the housing. As electrodes 194 and 196 are diametrically opposite to electrodes 180 and 182 the electrodes are separated by the center island 188. Electrode 194 is a well known type of silver chloride reference electrode and electrode 196 is a silver chloride electrode that is covered with a polytetrafluorethylene tubing so as to expose only the bottom cross-sectional surface area of electrode 196 to the first sample third portion and diluent.

During the titration process performed in the apparatus 157, housing 166 is rotated by motor 170 and drive belt 172 in order to cause the mixture of first sample third portion and diluent to flow in a circle around annular trough 186 in housing 166. The housing rotation and the testing at station 32 of the third portion of the first sample are performed simultaneously with the testing of the second portion of the first sample at the second testing location in carousel 118 of testing station 30 and the testing of the first portion of the first sample at the first testing location at carousel 68 of testing station 28.

As can be seen from the above explanation, the first, second and third portions of the first sample are each tested simultaneously at the respective testing stations 28, 30 and 32 by the particular testing apparatus. The tests are performed after the first sample has moved linearly and in a stepwise fashion along track 12 to read position 165, one position past the third location 144. The apparatus mechanics are synchronized so that when the sample reaches this read position, the first portion is located at the first testing location which is position 19 in carousel 68 of testing station 28; the second portion of the first sample is located in the second testing location which is the seventh location in carousel 118 of testing station 30 and the third sample portion is injected into or about to be injected into the apparatus 157 at the third testing station 32. The tests are all performed at the first particular time and the test results are coupled via the electronic circuitry to the appropriate readout devices shown at 34 so that the technician can look at the read position, identify the sample by the patient's identification number and simultaneously read all four measurements from readout devices 34.

In order to obtain a more clear understanding of the operation of the overall apparatus and of the tests performed by this apparatus, the following explanation of the testing structure, methods and circuitry at each of the testing stations 28, 30 and 32 are offered. Referring first to testing station 28 an analysis of the concentration of sodium and potassium ions in the first portion of the first blood sample is performed at this testing station. The diluent added to the blood serum sample is a mixture of predetermined concentration and volume including lithium, lithium carbonate, polyoxyethylene, an anti-foaming agent such as Anti-Foam B, a wetting agent such as Triton-X100 and water. It is well known in flame photometry that the intensity of the 671 nanometer wavelength light produced by burning lithium is proportional to the lithium concentration and that the intensities of the 589 nanometer and 768 nanometer wavelengths produced by burning sodium and potassium respectively are proportional to the concentration of sodium and potassium. With the relative light intensities being determinable photometrically and with a predetermined or known concentration of lithium being added to the blood sample, the concentrations of sodium and potassium can be electronically ascertained.

Certain of the elements noted as being added to the mixture perform special functions. Specifically, the Anti-Foam B prevents the contents of the containers from foaming and bubbling out of the container during the mixing process. The Triton-X100 promotes uniform droplet size formation within the flame photometer and the polyoxyethylene lowers the amount of atomized aerosol reaching the flame, thus reducing the amount of sodium reaching the flame.

During the testing procedure as previously explained, the mixture of serum and diluent at location nineteen in carousel 68 is aspirated to carburetor 86 in flame photometer 88 by way of tubing 84. Air under pressure is injected into carburetor 86 by tubing 89 and a gas used for igniting the mixture is coupled to flame photometer 88 by way of tubing 206. The air is passed through tubing 89 and carburetor 86 at 3,000 milliliters per minute (ml/min.) under 25 lbs. per square inch pressure causing the aspiration of 1.5 ml/min of sample. The air atomizes the sample and the atomized mixture is injected into a mixing chamber in section 208 of flame photometer 88. The gas is maintained in tubing 206 at a pressure of 17 lbs. per square inch and is passed through an aperture of fixed diameter into the mixing chamber with the fixed diameter aperture being used to maintain a gas delivery of 170 ml/min.

The atomized mixture of air and sample mixes with the gas with a substantial portion of this mixture dropping to a drain line 210 where it is drawn away to waste. A small potion of the atomized mixture rises and passes through a center opening 211 in a mounting block 212 and into a flame burner tube 214, about 1/200 ml/min of sample actually passing into burner tube 214. Burner tube 214 is shown in exploded view and it is to be understood that tube 214 mounts in opening 211. The burner tube 214 is of the Meker type so that the flame 216 formed at the top of burner tube 214 will be fairly widely dispersed creating uniform isotherms or heat areas which simplify photometric analysis.

An elongate cylindrical glass structure 218 shown in partial section and exploded, also is mounted on mounting block 212 and is coaxial with burner tube 214. Structure 218 forms a chimney surrounding burner 214. Air is forced into flame photometer 88 by way of fan 220 shown in the rear wall 222 of the flame photometer housing. This air feeds through air flow channels 224 in mounting block 212 and into the chimney space between chimney 218 and burner tube 216. The air flows up as a result of the pressure differential caused by fan 220 and acts to sheath the flame and cool the surrounding area. The heated air is exhausted out of the top of chimney 218.

Three air flow controlling structures 226 are shown mounted to burner tube 214. The air flow controlling structures 226 include a manner of fins 228 which extend radially into the chimney space defined between chimney 218 and burner tube 214. Each air flow controlling structure has the same number of fins, each aligned precisely with respect to one another. The fins of each air flow controlling structure 226 are vertically aligned with the fins of each other such structure. By providing these vertically aligned fins the air flowing through the chimney space in chimney 218 will be forced to flow therethrough in an extremely smooth and uniform laminar flow. This uniform laminar air flow substantially enhances the cooling efficiency so that burner tube 214 and the entire burner structure operates at a relatively cool temperature. The laminar air flow also produces a more stable flame which substantially enhances the ability to photometrically analyze the flame intensity. Furthermore, the laminar air flow and high efficiency cooling allow a reduced diameter chimney 218 to be employed thus reducing the size and space requirements of the flame photometer.

Figure 3:
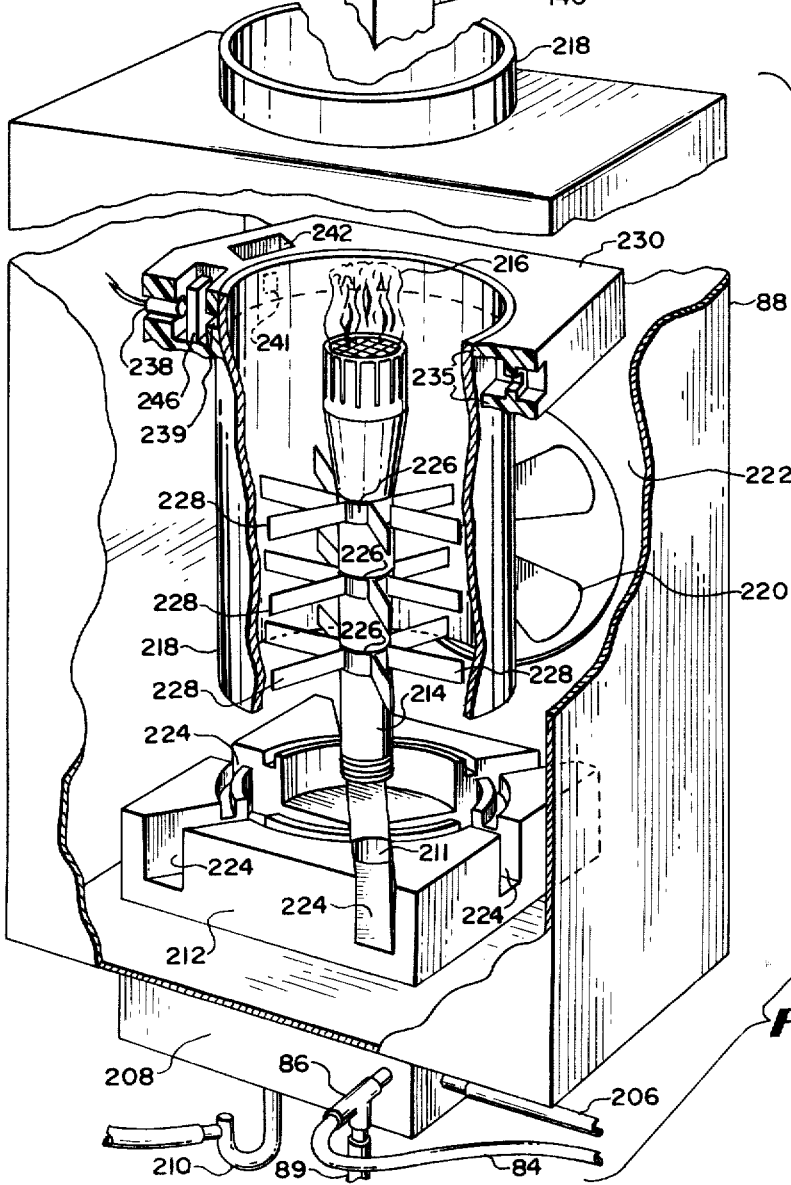
FIG. 3 is a perspective view of the flame photometer structure located at one station of FIG. 1 with a portion of the housing removed and with a portion of the structure shown in cutaway view.
Figure 4:
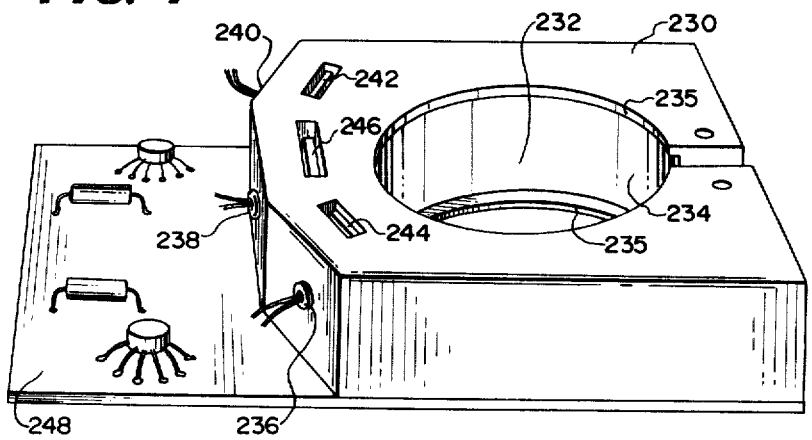
FIG. 4 is a perspective view of the light detector and flame photometer electronics shown partially in the cutaway view of FIG. 3.

A flame optical assembly 230 is shown mounted to the outer surface of glass chimney 218 at the flame height. This assembly is shown in cutaway view in FIG. 3 and is shown in perspective view in FIG. 4. Assembly 230 is a metallic block, preferably aluminum. A cylindrically shaped flame optical chamber 232 is formed in flame optical detector assembly 230. Flame optical detector assembly 230 is mounted to glass chimney 218 such that chamber 232 encircles and surrounds flame 216. The walls 234 of chamber 232 are blackened in order to minimize light reflection from flame 216. Three optical detectors 236, 238 and 240 are shown mounted into the side of assembly 230. In the preferred embodiment photodiodes are employed for reasons to be more fully explained in a subsequent portion of this application. It should be noted, however, that the photodiodes are capable of operating at very low intensities so that they may be employed effectively in a flame photometer. The three photodiodes are positioned so that the optical axis of each is radially disposed with respect to the center of optical chamber 232. In this manner the optical axis is aligned with the center of flame 216.

Three light filters 242, 244 and 246 are mounted in assembly 230, one each being inserted in front of a photodiode. Each filter passes only a specific light wavelength in order to pass only a specific wavelength to each photodiode. As noted earlier, the particular wavelengths emitted for sodium, potassium and lithium are 589, 768 and 671 nanometers respectively. The three filters 242, 244 and 246 are selected so that each one will transmit one of the three wavelengths. In the embodiment shown, filter 244 passes the sodium wavelength of 589 nanometers filter 246 passes the potassium wavelength of 768 nanometers and filter 240 passes the lithium wavelength of 671 nanometers.

In addition to being aligned radially with the center of chamber 232, the lenses on photodiodes 242, 244 and 246 are selected such that the angle of light acceptance for these photodiodes is 8° spherical. Consequently, the diodes cover a smaller angle of area at the center of the chamber and a smaller portion of the flame thus reducing the possibility of error due to a lack of uniformity in the various flame portions. The electronic circuit board 248 carrying the electronics connected to photodiodes 242, 244 and 246 and which operates on the signals therefrom in order to analyze the concentration of sodium and potassium in the blood sample is shown mounted to flame optical detector assembly 230.

Photodiodes 236, 238 and 240 are mounted in holes drilled through the side wall of optical detector assembly 230, the holes extending into flame optical chamber 232. These holes act as field stops for the photodiodes eliminating any extraneous light and allowing only the light from the flame 216 to reach the photodiodes. There is some quantum of efficiency variation in the diodes with the temperature variation of the diodes themselves. Mounting them in a solid metallic block such as assembly 230 causes them to be at substantially the same operating temperature so that the efficiencies are balanced with respect to one another. The walls 234 of of chamber 232 terminate at the top and bottom edge in lips 235 so that the chamber itself acts to form a light trap surrounding flame 216 when mounted to chimney 218.

Figure 6:
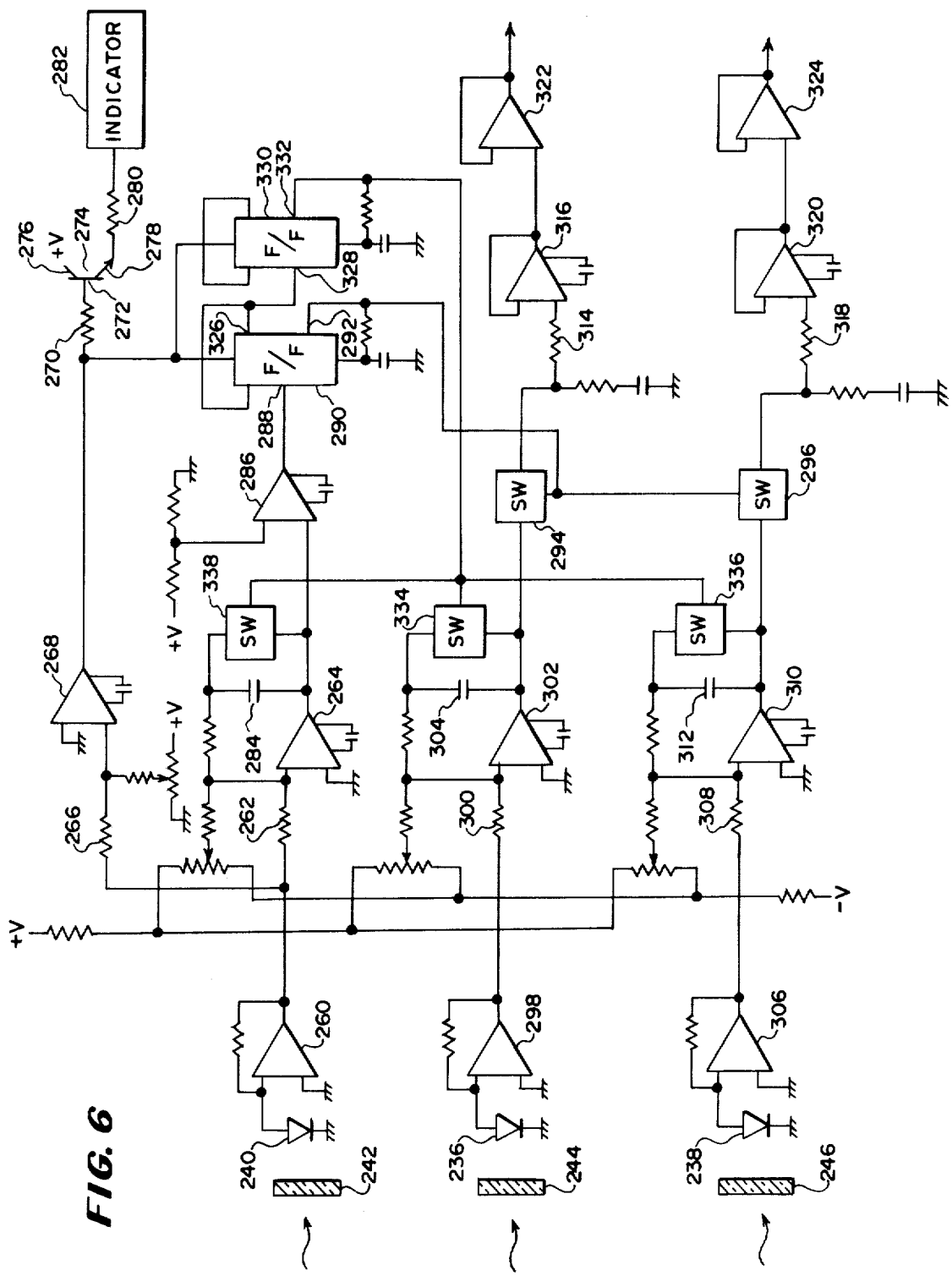
FIG. 6 is a combined schematic and block diagram of the electronic circuit for the flame photometer shown in FIG. 1.

Referring now to FIG. 6, the electronics employed in flame photometer 88 is shown in combined schematic and the block diagram form. As noted previously, light of specific wavelengths, produced by the burning of lithium, sodium and potassium, is passed through the appropriate filter 242, 244 and 246 respectively to its associated photodiode 240, 236 and 238 respectively. The photodiodes noted in this specific embodiment are PIN diodes. Each of the photodiodes 236, 238 and 240 is operated at a zero bias. When a zero bias is employed, a "dark current" through the diode is not created and the diode is approximately 80% efficient. By operating each at zero bias and eliminating dark current, any temperature dependency problems associated with PIN diodes is eliminated.

The 671 nanometer wavelength light produced by the burning lithium passes through filter 242 to photodiode 240 which produces the voltage that varies in accordance with the received light intensity. This voltage is coupled to amplifier 260 where it is amplified and coupled through resistor 262 to integration amplifier 264. The signal from amplifier 260 is also coupled through resistor 266 to amplifier 268 where it is amplified and coupled through resistor 270 to the base electrode 272 of transistor 274. The signal coupled to base 272 forward biases transistor 274 coupling a voltage from collector 276 to emitter 278, through resistor 280 to an indicator circuit 282. Indicator circuit produces a visual indication in response to this voltage so that a visual indication if provided of the presence of lithium in flame 216.

The signal coupled to integration amplifier 264 will be integrated to develop an integration voltage across integration capacitor 284. This integration voltage is coupled to one input of a comparator 286, the other input being coupled to a reference potential. When the integration voltage at one input of comparator 286 is below the reference potential at the second input, comparator 286 will develop a low state, or zero signal at its output. When the integration voltage developed across capacitor 284 and coupled to the first input of comparator 286 exceeds the reference signal coupled to the second input of comparator 286, comparator 286 will change states and develop a high state or one level signal that is coupled to the clock input 288 of a monostable multivibrator or flip-flop (F/F) 290.

Monostable multivibrator 290 when it receives a one level signal at the clock input 288 will change state and develop a high state or one level signal at the Q output 292, which is coupled to the control inputs of analog switches 294 and 296 resectively.

At the same time as the 671 nanometer wavelength produced by the burning lithium is coupled through filter 242 to photodiode 240, the 589 nanometer wavelength produced by the burning sodium is coupled through filter 244 to photodiode 236; and the 768 nanometer wavelength produced by the burning potassium is coupled through filter 246 to photodiode 238. The electrical signals developed by photodiodes 236 and 238 in response to the received wavelengths of light vary in accordance with the intensity of the received light.

The signals developed by photodiode 236 are coupled to amplifier 298 where they are amplified and coupled through resistor 300 to integration amplifier 302. Integration amplifier 302 integrates the signals received and develops an integration signal across integration capacitor 304.

The signals developed by photodiode 238 are coupled to amplifier 306 where they are amplified and the amplified signals coupled through resistor 308 to the input of integration amplifier 310. Amplifier 310 is identical to amplifiers 302 and 264 and integrates the signal received to develop an integration voltage across integration capacitor 312. The integration voltages developed across integration capacitors 304 and 312 respectively are porportional to the concentration of sodium and potassium respectively in the first portion of the first blood sample burnt in flame photometer 88. These signals are integrated in integration amplifiers 302 and 310 because integrating the signals over a time period cancels any noise effect which may occur due, for example, to the variations in flame in the flame photometer.

As noted previously, when the integration voltage developed across integration capacitor 284 reaches a predetermined level, indicating a known concentration of lithium has been burnt in the flame photometer, monostable multivibrator 290 changes states and develops a high state signal. This high state signal is developed for a predetermined period of time, in the preferred embodiment 3 milliseconds, and is coupled to switches 294 and 296. The signal coupled to switches 294 and 296 causes these two switches to close. The closing of switch 294 allows the integration voltage developed across capacitor 304 to be coupled through switch 294 and resistor 314 to an amplifier 316. The closing of switch 296 allows the voltage developed across integration capacitor 312 to be coupled through switch 296 and resistor 318 to amplifier 320. Amplifiers 316 and 320 will amplify the signals and couple them to buffer amplifiers 322 and 324 where they will be further amplified and compensated to provide an output in terms of specified units, for example, milliequivalents. The resultant signals are coupled to appropriate readout devices such as for example readout devices 34 shown in FIG. 1 to indicate the sodium and potassium content in the first sample of the first portion passed through flame photometer 88.

At the end of the noted three millisecond period, monostable multivibrator 290 is reset and the Q output 292 returns to a low state. This change in state is coupled to clock input 328 of a monostable multivibrator 330 causing monostable multivibrator 330 to change states and develop a high state signal at its Q output 332 for a 3 millisecond period. This high level signal is coupled from output 332 to the control inputs of switches 334, 336 and 338. Switches 334, 336 and 338 are connected in parallel with integration capacitors 304, 312 and 284 respectively. When a high state signal is received at the control inputs of switches 334 and 336, they will close producing a short circuit across integration capacitors 304, 312 and 284. The short circuit will cause the integration capacitors to discharge the voltage developed thereacross thereby resetting all three channels for a succeding measurement.

The test performed at station 30 is a coulometric titration of the second portion of the first sample of blood serum in order to determine bicarbonate content. The titration end points are determined photometrically so that the entire apparatus at this station 30 can be described as or defined as a photometric analysis apparatus.

At station 30, a predetermined amount and concentration of an aqueous solution of sodium nitrate and nitric acid is added to the second portion of the first sample in a cylindrical container 122 in carousel 118 by operation of diluter pump 108. This occurs at the first location in carousel 118, opposite the second location 90. When the first sample has been moved to the second location of carousel 118, pump 108 discharges a predetermined amount and concentration of an aqeuous solution of methanol, methylene blue, phenol red and sodium oxalate into the diluted first sample.

The addition of a known quantity of acid to the blood sample causes it to become acidic, producing a variation in the blood sample pH from the normal pH reading of 7.4 The acid itself creates a chemical reaction with the blood bicarbonate causing its disassociation into carbon dioxide and water. At carousel locations three, four, five and six air is injected into the diluted second portion of the first sample through pipettes 128. This air bubbles through the diluted sample allowing the carbon dioxide to leave the sample solution. At the end of this four step bubbling process, an acidic solution remains. Because a known quantity of acid diluent was initially added, and the solution is now known to be acidic, the solution can be titrated in a reverse manner in order to return the pH of the solution to 7.4. This titration can be accomplished coulometrically by passing current between the two copper electrodes 130. The passage of this current produces hydroxyl ions which combine with the chemicals in solution causing the mixture to become more alkaline, returning the solution to a pH of 7.4. Measurement of the electric current passed between the electrodes is a measurement of the amount of hydroxyl ions produced and is thus a measurement of the amount of carbon dioxide and the bicarbonate which produced the carbon dioxide.

Although the above noted test procedure for bicarbonate is considered to be a relatively standard test, means for determining the test end point or when the titration process has returned the solution to a pH of 7.4 have varied substantially from system to system, some systems being adequate although not precise and accurate, and some systems being wholly inadequate. One system heretofore employed utilizes photometric analysis in order to determine end point. In this system phenol red of known concentration is added to the sample to be analyzed. It is known that phenol red is yellow in color when in an acid solution and red in color when in an alkaline solution. As the solution goes from acid to alkaline and the phenol red becomes more red, it absorbs the green wavelength of light to a greater and greater degree. When a known concentration of phenol red is employed, a known absorbance of green light occurs at various levels of relative acidity or alkalinity (pH). The system simply passes a green light through the sample to which a predetermined amount and concentration of phenol red had been added. A photodetector receives the green light and develops a voltage which varies in accordance with the intensity of the received light. The titration process of a sample is initiated and, as the solution reduced in acidity and approaches the normal pH of 7.4, the light flux and resultant voltage drops. When the voltage reaches a predetermined level, presumably calibrated to correspond to a pH of 7.4, an indication is provided to stop the titration operation.

In the system just described, use of a single dye is acceptable if light of a known intensity is provided at all times. Furthermore, the vessel location and/or size has to be fixed precisely so that the path length through the solution is fixed. Any variation in intensity of the light and/or in path length will reduce the accuracy of the answer. Any turbidity of the sample or the presence of certain elements which are not altogether uncommon in the blood and which tend to absorb light at the desired wavelength, will also reduce the accuracy of the answer.

In some systems a somewhat higher level current is provided between the electrodes initially with the amount of current supplied decreasing as complete titration is approached. This tends to eliminate overshoot problems which occur when a constant amount of current is supplied until the entire titration process is complete and then the current is terminated.

In the method and apparatus of the instant application, two dyes are employed for end point determination of the bicarbonate titration at station 30. Two dyes are employed in order to eliminate the problems of inaccuracy due to variation in light intensity, turbidity, container positioning and path length. The dyes employed are methylene blue and phenol red. Both are added in a known concentration, at least with respect to one another. The methylene blue employed has an absorption maxima at the red wavelength. This absorption maxima is independent of the acidity or alkalinity of the solution in container 122. As noted earlier, phenol red has an absorption maxima at the wavelength of green light and the amount of absorption will vary in accordance with the acidity or alkalinity of the mixture in container 122.

The absorbance of the methylene blue at the red wavelength will be proportional to the path length through the solution, the concentration of methylene blue in the solution and what is known as the extinction coefficient of methylene blue, a number which is known and is directly related to the characteristics of methylene blue. With phenol red, the absorbance will be proportional to path length, concentration, extinction coefficient and the solution pH. If green and red wavelengths of light are passed through the solution to be analysed along the same path so that the path length for both light wavelengths is identical, and if the ratio of the relative light absorbances through the solution at the red wavelength and at the green wavelength is taken, the variances due to path length, concentration and extinction coefficient will be eliminated because all are either equal or of known relationship to one another. Consequently, the ratio taken will be proportional only to pH of the solution. If a particular solution pH is desired, a particular ratio of absorbance for methylene blue and phenol red can be selected and employed to obtain a titration end point with that particular pH.

The concentrations of the dyes can be adjusted so that any desired ratio will yield the desired pH. The absorbance measurement normally employed for end point determination is a logarithmic function which normally must be converted to the antilog equivalent in order to provide a number or reading which is meaningful and which can be used in order to identify end point and terminate the titration process. If a ratio of absorbances is employed the antilog must still be taken. However, if concentrations are selected such that the ratio of absorbances at the selected wavelengths is 1, no antilog conversion is necessary because the log of 1 is zero and the logarithmic function portion of the absorbance measurement reduces to zero. Under these conditions only a simple comparison measurement of the absorbance at the selected wavelengths is necessary.

In the method employed herein, a known concentration of phenol red and methylene blue is added to a known quantity of acid, water and the second portion of the first sample. The concentration of methylene blue is selected such that light at the red wavelength is 70% absorbed by passage through the container 122 in carousel 118. The transmitted light is coupled to a photodetector for developing a voltage proportional to the intensity of transmitted light. The concentration of phenol red added to the sample is selected such that when the sample has been titrated so that the pH is returned to 7.4, the absorbance through the container 122 in carousel 118 at the green wavelength also is 70%, the sample in the container 122 having a lesser absorbance of the green wavelength before the titration process has returned the solution to a pH of 7.4. Consequently, when the absorbance at the green and red wavelength are identical, the titration process is completed and the amount of current supplied in the titration process can be measured to evaluate the amount of hydroxyl ions added, and consequently the amount of bicarbonate originally in the sample.

Figure 7:
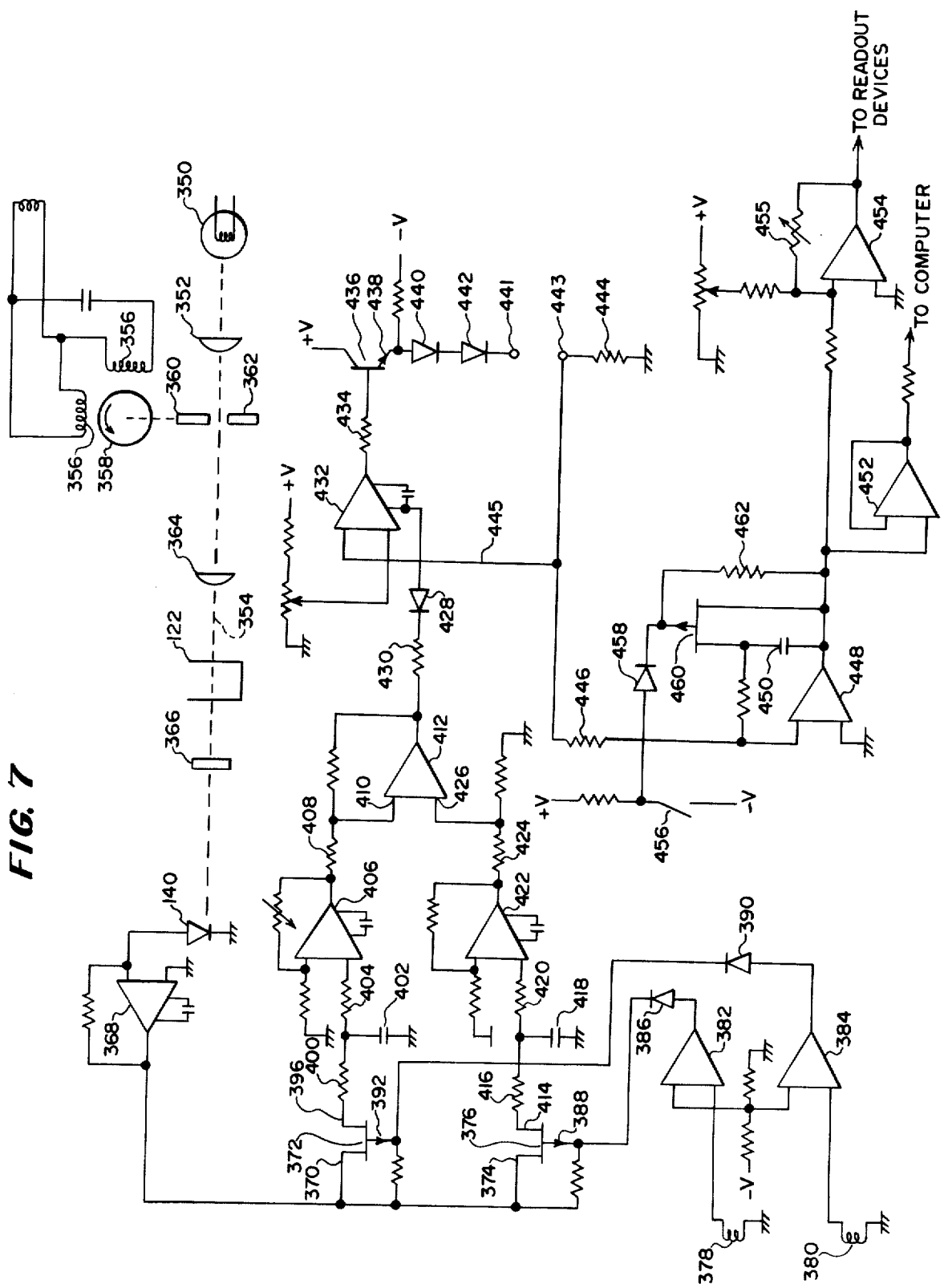
FIG. 7 is a schematic diagram of the optical system employed in the photometer apparatus located at the second station in FIG. 1, combined with a schematic and block diagram of the electronic circuitry employed by the photometric apparatus at the second station of FIG. 1.

Referring now to FIG. 7, a lamp 350 is shown for providing the light to be passed through the container 122. Lamp 350 is mounted in light source 140 at second testing station 30. A condenser lens 352, also mounted in light source 140, concentrates and focuses the light produced by lamp 350 along the path shown by the dotted line 354. A motor, shown represented by motor coils 356, rotates a chopper wheel shown schematically at 358 which is positioned in light path 354.

Chopper wheel 358 also is situated in light source 140 and has two filters positioned diametrically opposite to one another thereon. One filter thereon, the red filter, passes a light wavelength of 615 nanometers and is identified by the reference number 360; the other filter passes only the green wavelength of 570 nanometers and is represented by the number 362. Rotation of chopper wheel 358 causes the red and green filters to alternately pass into light path 354 so that the light passed through chopper wheel 358 alternates between the light of red wavelength and the light of green wavelength. This light follows the dotted line path 354 to a focusing lens 364, located in light source 140, which focuses the light into and through the container 122 at the seventh location on carousel 118. It is to be understood that containers 122, at least in position surrounding light path 354, are transparent to the light wavelengths passed.

Part of the light at both wavelengths is absorbed by the contents of container 122 as noted previously. The light transmitted through container 122 passes along path 354 to a filter 366 which blocks extraneous light and light of other frequencies. The light passing through filter 366 passes to the photodetector 142 shown in FIG. 2 and shown as a photodiode in FIG. 7.

The light received by photodiode 142 produces a voltage which varies in amplitude in accordance with the intensity of the alternately received red and green wavelength light. Because the light received has passed through chopper wheel 358 in order to produce the alternately time spaced green and blue wavelength light along path 354, the signals developed across photodiode 142 appear to be separate pulses. These pulses are coupled to an amplifier 368 where they are amplified and coupled to the drain 370 of a field effect transistor (FET) 372 and the drain 374 of a FET 376.

A magnet is positioned on chopper wheel 358 adjacent to red filter 360. As chopper wheel 385 rotates within light box 140 the magnet passes a green magnetic pickup coil 378 and one half cycle later it passes a red magnetic pickup coil 380. The green magnetic pickup coil will develop a voltage thereacross when the green filter passes through the light beam, and the red pickup coil will develop a voltage thereacross when the red filter passes through the light beam.

The voltage developed by pickup 378 is coupled to amplifier 382 and the voltage developed by pickup 380 is coupled to amplifier 384. Both of these amplifiers are of the comparator type and respond to the voltage coupled from their respective magnetic pickup to change states switching from a high state signal to a low state signal at their outputs. The low state signal developed by amplifier 382 reverse biases diode 386. When diode 386 is reverse biased the voltage at drain 374 and gate 388 of FET 376 is equal so that FET 376 becomes conductive. The low state signal developed by amplifier 384 reverse biases diode 390. When diode 390 is reverse biased the potential between drain 370 and gate 392 is zero so that FET 372 becomes conductive. FETS 372 and 376 then are alternately biased on and off, 372 being biased on when light of red wavelength is passed through red filter 360 in chopper wheel 358 and FET 376 being biased on when light of green wavelength is passed through filter 362 in chopper wheel 358. With this synchronization of FET 372 conductivity with the red light passed and FET 376 conductivity with the green light passed, FET 372 passes only pulses produced by light of red wavelength and FET 376 passes only pulses produced by light of green wavelength.

The pulsed passed through FET 372 are coupled from source 396 of FET 372 through resistor 400 to a sample and hold circuit including capacitor 402, resistor 404 and amplifier 408. Capacitor 402 charges to a voltage that is proportional to the amplitude of the received pulse and therefor proportional to the intensity of the received light wavelength. The voltage developed across capacitor 402 is coupled through resistor 404 to amplifier 406. Amplifier 406 amplifies the voltage and couples the amplified voltage through resistor 408 to the negative input 110 of a differential amplifier 412.

The signals passed through FET 376 are coupled from source 414 of FET 376 through resistor 416 to a sample and hold circuit including capacitor 418, resistor 420 and amplifier 422. Capacitor 418 is identical to capacitor 402 and will develop a voltage thereacross which is proportional to the amplitude of the received pulse and therefore proportional to the intensity of the received light wavelength. The signal developed across capacitor 418 is coupled through resistor 420 to amplifier 422 where it is amplified and the amplified signal is coupled through resistor 424 to the plus input 426 of differential amplifier 412.

When the input voltage to input 410 is less than the input voltage to input 426 of amplifier 412, thus indicating that there is a greater absorbance of the red wavelength light than of the green wavelength light, and indicating an acidic solution which has not returned to a pH of 7.4, amplifier 412 is in an on state with a high state signal at the output. With a high state signal present at the output of amplifier 412, diode 428 is reverse biased through resistor 430. With diode 428 nonconductive, amplifier 432 develops a predetermined voltage at its output which is coupled through resistor 434 to the base electrode of transistor 436 rendering transistor 436 conductive. With transistor 436 conductive, a constant titration current flows from emitter 438 of transistor 436 through diode 440 and light emitting diode 442, to terminal 441, through terminal 441 to one electrode 130 connected thereto, through electrodes 130 in the solution causing titration to continue to terminal 443 connected to the other electrode 130, and from terminal 443 through resistor 144 to ground potential. The voltage developed across resistor 440 is coupled back to a second input of amplifier 432 by way of conductor 445 in order to provide a positive feedback for maintaining a constant current across electrodes 130.

Light emitting diode 442 illuminates in response to the current passed therethrough providing a positive visual indication of the presence of titration current.

The voltage developed across capacitor 418 in the sample and hold circuit reduces in amplitude with a reduction in acidity of the sample solution and an approach towards sample pH of 7.4. This results from a reduction in the intensity of the green light, an increase in the absorbance of the green light wavelength by the solution, and a reduction in developed voltage. With a reduction in voltage across capacitor 418 voltage at input 426 reduces and approaches the voltage at input 410 of differential amplifier 412. As voltage at input 426 approaches the voltage at input 410, the output of amplifier 412 begins to change from a high state signal to a low state signal. The change from a high state signal at the output of amplifier 412 to a low state signal, although not instantaneous, does not take an appreciable period of time. This change will occur when titration is almost completed, lasting for a period constituting approximately 5 percent of the total titration time period.

As the output of amplifier 412 changes from a high state to a low state signal diode 428 begins to forward bias. As diode 428 forward biases it bleeds away a small amount of the current in amplifier 432 causing a reduction in the constant current supplied to and through electrodes 130. As the voltage at the output of amplifier 412 continues to approach zero, diode 428 will become more conductive further bleeding the current away from amplifier 432 and reducing the current coupled through electrodes 130 until all of the current passed through the electrodes is terminated thus terminating titration.

Generally in prior art systems the time period during which titration current is passed through the electrodes in solution is measured and this time period is indicative of the bicarbonate concentration. In such systems, however, the current magnitude is constant during the entire titration process. If the current amplitude is varied during the titration process as is the case in the instant apparatus, the amount of current supplied must be integrated over the time period of the titration process in order to ascertain the bicarbonate concentration.

Referring again to FIG. 7, the voltage developed across resistor 444 is proportional to the constant titration current passing through resistor 444. This voltage is coupled through resistor 446 to the input of integrated amplifier 448. The signal coupled thereto is integrated in order to develop an integration voltage across integration capacitor 450. This integration voltage, which is inversely proportional to bicarbonate concentration, is coupled to buffer amplifiers 452 and 454 where the signals are amplified. The amplified output of amplifier 454 is coupled to visual display devices such as devices 34 in FIG. 1 for observation by a technician and the output of amplifier 452 is coupled to a computer where the patient's bicarbonate concentration is permanently recorded. Amplifier 454 may be adjusted by potentiometer 455 so that the signal coupled to devices 34 will provide a reading in the desired units, for example, milliequivalents.

At the end of the measurement cycle and prior to the insertion of a new sample and diluent, the control system in the apparatus actuates a reset switch 456. When reset switch 456 is actuated, it closes reducing the voltage coupled to diode 458 and rendering diode 458 non-conductive. With diode 458 rendered non-conductive field effect transistor (FET) 460 is rendered conductive by the bias provided through resistor 462 between the drain and gate. With FET 460 conductive a short circuit is provided between the drain and the source. As FET 460 is connected in parallel with integration capacitor 450, integration capacitor 450 being coupled between the drain and the source of FET 460, the forward biasing of FET 460 provides a short circuit path across capacitor 450 causing the capacitor to discharge the integration voltage developed and resetting the circuit for a subsequent test procedure.

At station 32 a coulometric titration of the third portion of the first blood sample is performed for determining the chloride concentration in the blood sample. The titration method generally employed for determining chloride is known as the Cotlove titration method, and the method employed herein is somewhat similar to this well known method.

In the standard Cotlove titration method, two sets of silver electrodes are employed, one set as the indicating electrode pair and the other set as the titrating electrode pair. The blood sample to be analysed is placed in a container along with an aqueous solution of acetic acid and nitric acid and gelatin. The acids participate in the chemical reaction while the gelatin acts to assure uniform removal of silver from particular electrodes. The indicator electrodes are forward biased by use of a battery and a control circuit is connected in series with the battery, the control circuit being connected to a current source in series with the silver titration electrodes.

The chloride in the blood sample forms a silver chloride surface or skin around the positive indicating electrode in the mixture. This skin acts in the same manner as an opposing voltage to the polarizing voltage of the battery thus preventing the passage of current between the two indicating electrodes. When the current between the two indicating electrodes drops to zero, the control circuit allows the current source coupled to the titrating electrodes to pass a predetermined current through the electrodes. Passage of current through the silver electrodes causes the release of silver ions into the solution. These silver ions react with the solution and particularly with the chloride ions forming the skin surrounding the positive indicator electrode to form silver chloride in solution. The silver chloride is held in solution by the acetic acid.

As the silver chloride in solution forms, the skin surrounding the positive indicator electrode is exhausted by the removal of chloride. At a particular point the skin surrounding the electrode simply falls off of the positive indicator electrode allowing the battery to forward bias and pass current between the two indicator electrodes. When current passes between these two indicator electrodes, the current circuit terminates further passage of constant current to the silver titration electrodes. The time during which the current is supplied to the silver titration electrodes is measured and is proportional to the concentration of chloride in the solution.

The method described above takes approximately one hundred seconds for a complete titration. In that method the titrating current is supplied by a constant current generator and continues at a constant current level until the control circuit indicates titration is complete. Because the operation is in the nature of a feedback circuit, some additional current is passed after titration is completed. If, for example, one half second of additional current is supplied, the error would be in the order of 0.5 percent which is not serious. However, if it was desired to titrate in, for example, a 15 second period, then the delay in terminating current of, for example, 0.5 percent would yield a 3 or 4 percent error which is excessive. In an automated system it is desirable to perform the chloride titration procedure in approximately 15 seconds while still maintaining an accuracy of 0.5%.

A second problem associated with the above noted method is that the indicator electrodes require a specific amount of time to regenerate and return to a useable condition after each titration process. If, for example, the titration process itself takes in the neighborhood of 100 seconds, it also may take in the neighborhood of 100 seconds for the titration electrodes to regenerate and return to a state which allows a succeeding titration to be effected with some degree of accuracy. Passage of current between the electrodes causes sulfide and other comtaminants to build up on an electrode further inhibiting regeneration. In an automatic testing apparatus it is desirable to eliminate this delay in processing due to electrode regeneration.

Another problem associated with the above described method is that the two pairs of electrodes are in somewhat close physical relationship with one another during a titration process. This occurs because the amount of sample and diluent employed is rather small, and the container holding this small mixture is relatively small. A device also must be inserted into the container in order to provide mixing of the fluid therein during the titration process. With a mixing structure and four electrodes inserted into the container, by necessity all of these structures are in relatively close contact with one another. The close contact of the electrodes can result in an interaction between the electrodes during the titration process which reduces the accuracy of measurements taken. Furthermore, the mixing device employed is generally rather inefficient, and with the close spacing of the titration and indicator electrodes, an improper analysis due to inefficient mixing during the titration process can result. Inefficiency will effect the accuracy of the test results.

Referring now to FIGS. 1 and 5, an apparatus shown at station 32 performs a chloride titration. A cylindrical housing 166 is provided having an annular trough 186 formed therein. The third portion of the first blood sample is fed into the annular trough along with the desired amount of diluent consisting of an aqueous solution of acetic acid, nitric acid and gelatin. Housing 166 is rotated by motor 170 and the drive belt 172 causing the mixture in annular trough 186 to flow in a circle about the trough. This circular flow produces a mixing in the fluid, particularly as the titration process progresses, thus promoting rapid, uniform dispersion of the silver chloride throughout the fluid as the titration progresses. The rods 190, secured to housing cover 174 and extending into the fluid, act to disturb the fluid flow and further enhance the mixing action described so that an extremely uniform dispersion of the silver chloride is produced as the titration process progresses. The titration electrodes 180 and 182 are disposed at one point in the annular trough and aligned with a plane through their axis perpendicular to the housing radius and the indicating electrodes 194 and 196 are disposed at another point in the annular trough diametrically opposite to titration electrodes 180 and 182 and aligned with a plane through their axis which extends radially from the housing center. When spaced and oriented in this fashion, center island 188 separates the pairs of electrodes physically and the circular path formed by the fluid results in an extended electrical path which separates the electrodes electrically, and the orientation decreases electrical field interaction. Because of physical and electrical separation, substantially little interaction occurs between the titration electrodes 180 and 182 and the indicator electrode 194 and 196 so that the accuracy of the testing procedure is maintained.

In order to avoid the problem of excessive time delay due to electrode regeneration, a new approach to the indicator system and method and to the indicator electrodes is employed. Rather than pass a current between a pair of indicator electrodes and inhibit the current while silver is being released into the fluid so that silver chloride can be formed, a potential difference is maintained between the indicator electrodes. One electrode, 194 in FIG. 5, is a glass bodied, low leakage silver chloride reference electrode. Such electrodes are commercially available and provide a small path therethrough for ion travel. The ion travel, although very small, produces a potential which is a very stable reference potential against which a silver chloride electrode can be measured. The other is a silver chloride electrode which is sensitive to chloride and produces a voltage that is proportional to the chloride concentration.

As substantially no current is passed between electrode 194 and the second indicator electrode 196 the silver chloride sensing area is not disrupted to any substantial degree. Additionally, sulfides and other contaminants will not attach to the electrode causing a reduction in operating efficiency.

The second electrode as noted previously is of silver and is surrounded with a polytetrafluorethylene shield, except at its very tip so that only the tip is exposed to the fluid. The tip is treated by emersion in potassium chloride and current passage therethrough so that the tip forms a silver chloride electrode. Because only a very small silver chloride area is exposed to the solution response time of the electrode is substantially shortened.

Figure 8:
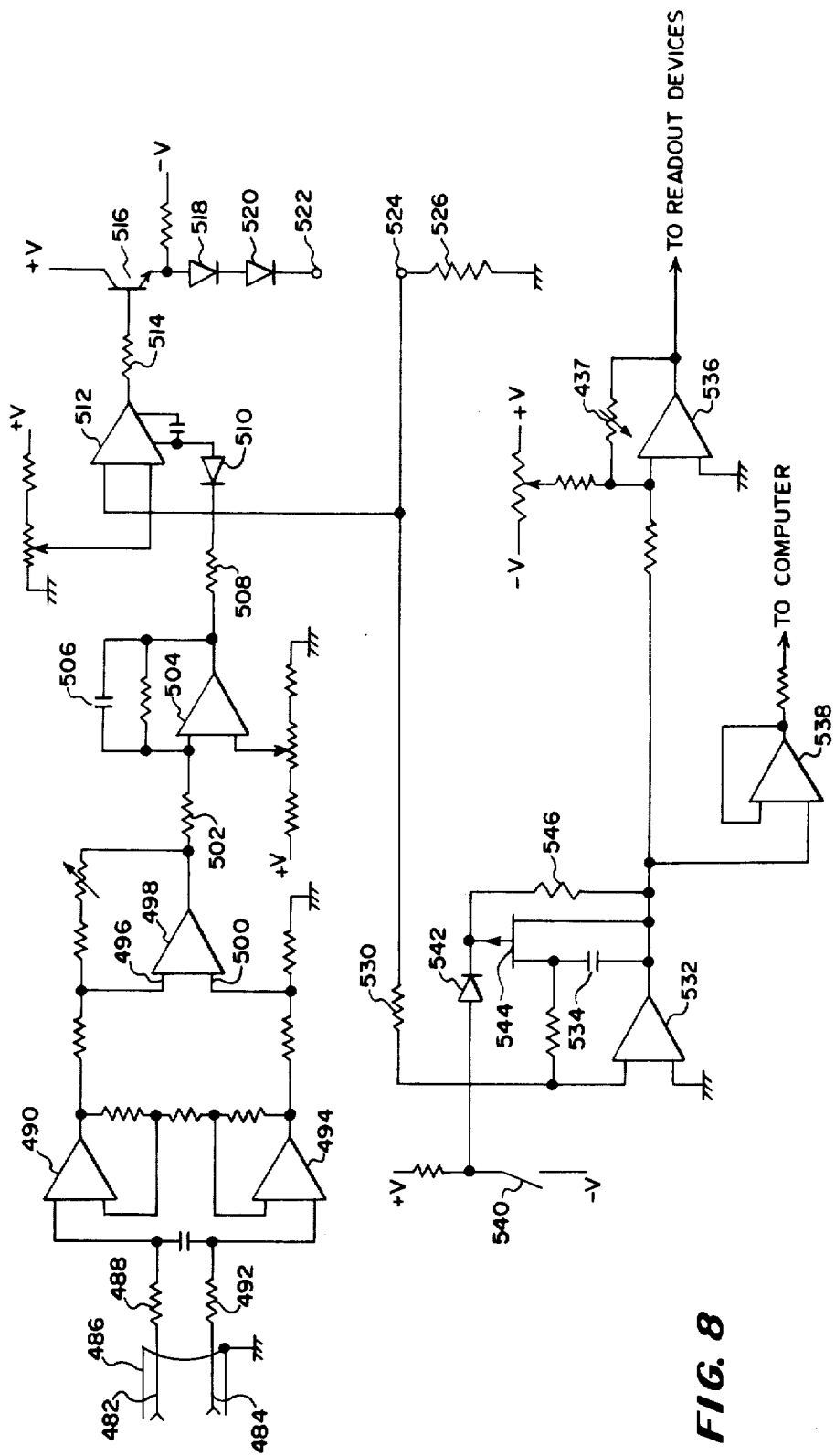
FIG. 8 is a combined schematic and block diagram of the electronics employed by the titration device shown at the third station of FIG. 1.

Referring now to FIG. 8, the indicator electrodes are connected to the electrical titration and measurement circuit shown therein and referenced generally by the number 480. Silver chloride reference electrode 194 is coupled to conductor 482 and silver chloride electrode 196 is coupled to conductor 484, both conductors being a part of a twisted, shielded pair identified by the reference number 486.

When the reference electrodes 194 and 196 are in the mixture of the first simple portion and diluent, reference electrode 194 will develope a potential which is coupled from conductor 482 through resistor 488 to one input of an amplifier 490 and silver chloride electrode 196 will develop a potential which is coupled from conductor 484 through resistor 482 to one input of an amplifier 494. The amplified signal developed by amplifier 490 is coupled to a negative input 496 of an amplifier 498 and the amplified signal developed by amplifier 494 is coupled to a positive input 500 of amplifier 498.

Amplifiers 490, 494 and 498 form a high impedance differential amplifier. In the specific embodiment shown, at the beginning of a titration process when the third portion of the first sample and the diluent are added into the annular trough 186 in housing 166, the voltage differential produced by indicator electrodes 194 and 196 will result in a voltage differential of approximately 480 milivolts between inputs 496 and 500. The high impedance amplifier consisting of amplifiers 490, 494 and 498 provides a gain of approximately 11 so that at the beginning of a titration process, the voltage at the output of amplifier 498 is approximately 5 volts. When the titration progresses to completion, the voltage difference between inputs 496 and 500 will increase to 600 milivolts.

The signal developed at the output of amplifier 498 is coupled through resistor 502 to one input of comparator 504, the second input of comparator 504 being coupled to a reference potential. At the beginning of a titration process, when the voltage developed at the output of amplifier 498 is approximately 5 volts, the difference in voltage at the two inputs of comparator 504 will cause the comparator to develop a high state or one level signal at its output. As the titration process progresses and approaches completion, the increased voltage developed at the output of amplifier 498 and coupled to the negative input of amplifier 504 will cause comparator 504 to change states with the output thereof changing from a high state to a low state signal. A feedback resistor 506 adds a certain amount of hysteresis or delay to the switching operation of the comparator 504 so that the transition from a high state signal to a low state signal is not instantaneous. The change from a high state to a low state signal at the output of amplifier 504 lasts for approximately the last 5% of the titration period allowing a gradual reduction in the titration current so that the end point titration is reached at a low current level and titration beyond the desired end point is avoided.

At the beginning of the titration process, and during approximately 95 percent of the titration process, a high state signal will be present at the output of comparator 504. This high state signal will be coupled through resistor 508 to diode 510 reverse biasing diode 510. When diode 510 is reverse biased, amplifier 512 is operative to couple a predetermined voltage through resistor 514 to the base electrode of transistor 516. The voltage coupled to the base electrode of transistor 516 will render transistor 516 conductive allowing a predetermined constant titration current to flow through diode 518 and light emitting diode (LED) 520, to terminal 522, from terminal 522 through one silver titrating electrode 180 connected to terminal 522 and through the solution between electrode 180 and 182, causing titration to progress, to terminal 524 connected to the other silver titrating electrode 182 and from terminal 524 through resistor 526 to ground potential. A feedback loop provided by conductor 528 between terminal 524 and one input of amplifier 512 provides a voltage feedback which corresponds to the current flow through resistor 526 and titrating electodes 180 and 182. This voltage feedback acts to maintain the current path through the electrodes at a constant current level.

The current flowing through LED 520 causes the LED to illuminate and provide a visual indication of current flow in the path. As LED 520 is in series with titrating electrodes 180 and 182 it provides a positive indication that titration of the liquid is occurring.

As the output of comparator 504 changes from a high state to a low state signal, the voltage coupled through resistor 508 to diode 510 causes diode 510 to slowly become forward biased. As diode 510 forward biases, it bleeds the current from amplifier 512. The reduction in current in amplifier 512 reduces the voltage coupled to the base of transistor 516, thus reducing the current flow through titration electrodes 180 and 182. As noted previously, this current reduction occurs during the last 5 percent of titration and, as diode 510 becomes fully forward biased at the end of titration, it bleeds sufficient current from amplifier 512 to reduce the voltage to the base electrode of transistor 516 to a point which renders the transistor 516 nonconductive. When transistor 516 becomes nonconductive all current through electrodes 180 and 182 stops and the titration process terminates.

In the titration process for measuring chloride, the amount of current passed between the titrating electrodes and the time period for which this current is passed is proportional to the amount of silver ions released and is also proportional to the amount of chloride ions present. Generally, in prior art systems the time period during which titration current is passed through the electrodes in solution is measured and this time period is indicative of the chloride concentration. In such systems, however, the current magnitude is constant during the entire titration process. If the current amplitude is varied during the titration process as is the case in the instant apparatus, the amount of current supplied must be integrated over the time period of the titration process in order to ascertain the chloride concentration.

Referring again to FIG. 8, the voltage developed across resistor 526 is proportional to the constant titration current passing through resistor 526. This voltage is coupled through resistor 530 to the input of integration amplifier 532. The signal coupled thereto is integrated in order to develop an integration voltage across integration capacitor 534. This integration voltage, which is proportional to chloride concentration, is coupled to buffer amplifiers 536 and 538 where the signals are amplified. The amplified output of amplifier 536 is coupled to visual display devices such as devices 34 in FIG. 1 for observation by a technician and the output of amplifier 538 is coupled to a computer where the patient's chloride concentration can be permanently recorded. Amplifier 436 may be adjusted by potentiometer 437 so that the signal coupled to the readout devices will provide a reading in the desired units, for example, milliequivalents.

At the end of the measurement cycle and prior to the insertion of a new sample and diluent, the control system in the apparatus actuates a reset switch 540. When reset switch 540 is actuated, it closes reducing the voltage coupled to diode 542 and rendering diode 542 nonconductive. With diode 542 rendered nonconductive field effect transistor (FET) 544 is rendered conductive by the bias provided through resistor 546 between the drain and gate. With FET 544 conductive a short circuit is provided between the drain and the source. As FET 544 is connected in parallel with integration capacitor 534, integration capacitor 534 being coupled between the drain and the source of FET 544, the forward biasing of FET 544 provides a short circuit path across capacitor 534 causing the capacitor to discharge the integration voltage developed and resetting the circuit for a subsequent test of procedure.

Although the control system for actuating the hydraulic pistons and for operating the apparatus at testing stations 28, 30 and 32 has not been shown, it is to be understood that any one of a number of control systems, well known in the art, may be employed. For example, a number of adjustable cams may be mounted on a rod whch is rotated at a predetermined speed by a motor. The cams may be coupled to mechanical actuators and electrical switches for actuating the hydraulic pistons and testing apparatus. The cams are each individually adjusted in order to obtain the timed and synchronized operation heretofore described. Determination of proper adjustments, timing and synchronization for operating the overall apparatus is believed to be relatively simple for a technician after reading the above material.

As can be seen then an improved blood electrolyte analysis apparatus has been provided which simultaneously provides the test results for the four primary blood electrolytes. The tests are performed simultaneously with various parts of the overall apparatus operating in synchronism in order to provide simultaneous testing and output readings. This simultaneous operation and synchronism reduces the complexity of the apparatus and the amount of equipment necessary. The individual testing apparatus employed at each testing station within the overall apparatus employ methods and structures which yield greater accuracy and precision than heretofore possible while performing the tests in a very short time period so that the overall apparatus may be used in emergency procedures. Of course, other body fluids can be tested, such as, urine, cerebrospinal fluid, and transudates and exudates.

Although a specific embodiment of the overall apparatus has been shown and described and specific embodiments of the testing apparatus and testing methods at each testing station has been shown and described, it should be readily recognized that a number of variations and modifications may be made in the invention without departing from the spirit and scope thereof as defined in the appended claims.

What it is claimed and desired to secure by Letters Patent of the United States is:

1. An apparatus for testing a body fluid, such as for blood electrolytes in a blood sample including in combination;

means for moving a plurality of blood samples serially and in a linear manner along a track from an input to an output, a first testing station for testing at least a first sample constituent, said first testing station including means for removing a first portion of said sample at a first location along said track, first rotating means for receiving and storing said first portion in a container and for rotating said container to a first testing position at a first time, first testing means for testing said first portion while at said first testing position, a second testing station for testing a second sample constituent, said second testing station including means for removing a second portion of said sample at a second location along said track, a second rotating means for receiving and storing said second portion in a container and for rotating said container to a second testing position at said first time, second testing means for testing said second portion while at said second testing position, a third testing station for testing a third sample constituent, said third testing station including means for removing a third portion of said sample at a third location along said track and testing means for receiving said third portion and operative to test same at said first time whereby said first, second and third tests are performed simultaneously, and output means coupled to said first, second and third testing stations for simultaneously providing said test results.

2. The apparatus of claim 1 wherein said first rotating means includes a first carousel having a plurality of containers circularly disposed therein for storing first portions of a sample and first index means for imparting a stepwise circular rotation to said carousel to rotate said container to a first receiving location aligned with said first location and to said first testing position at said first time thereafter, said second rotating means include a second carousel including a plurality of containers circularly disposed thereon for storing second portions of a sample and second index means for imparting a stepwise circular rotation to said carousel to rotate said containers to a second receiving location, aligned with said second location and to said second testing position at said second time thereafter.

3. The apparatus of claim 2 wherein said first and second index means are synchronized for simultaneous operation for simultaneously rotating said first and second carousels.

4. The apparatus of claim 3 wherein said first carousel has 24 containers and said second carousel has 12 containers.

5. The apparatus of claim 4 wherein said means for moving a plurality of samples serially along a track include holder means seated on said track for separately holding each of said samples and third index means for moving said holder means in a stepwise linear manner along said track for passing a particular sample to said first location, to said second location and to said third location.

6. The apparatus of claim 5 wherein said third index means indexes twelve times from said first to said second location and six times from said second to said third location.

7. The apparatus of claim 4 wherein said third index means is synchronized with said first and second index means.

8. The apparatus of claim 7 wherein said first, second and third tests are performed following the nineteenth index of said first index means after said means for removing a first portion tested in said first testing means.

9. The apparatus of claim 1 wherein said first testing means include flame photometer means for measuring said first sample constituent, said flame photometer means including first input means for receiving said first portion of said sample from said first rotating means, second and third input means for receiving gases to mix with said first portion for igniting the same, a burner tube for burning said sample and the gases, chimney means surrounding said burner tube, a source of air coupled to said chimney means for passing gas through said chimney surrounding and along said burner tube for cooling same, and means secured to said burner tube and disposed between said tube and chimney means along the length of said tube for producing a laminar flow of said air passing through said chimney means.

10. The apparatus of claim 1 wherein said first testing means include flame photometer means for measuring said first sample constituent, said flame photometer means including chimney means, a burner tube disposed within said chimney means and including an input end for receiving sample and gases to be burned and a burner end whereat said gases and sample are burned producing a flame, means for coupling air through said chimney means for passing same through said chimney means and along said tube, air flow control means secured to said burner tube at a plurality of locations therealong, said air flow control means controlling said air flow through said chimney means and creating a laminar air flow therethrough for cooling said chimney means and tube.

11. The apparatus of claim 10 wherein said air flow control means each include a plurality of fins radially disposed in said chimmey means about said tube, said fins of each said air flow control means being aligned with the fins of each other of said air flow control means whereby uniform laminar flow of said air is created.

12. The apparatus of claim 11 wherein said chimney means is an elongate glass cylinder.

13. The apparatus of claim 11 wherein said flame photometer includes light detection means secured to said chimney means adjacent said burner and detecting said flame and flame intensity.

14. The apparatus of claim 13 wherein said chimney means is an elongate glass cylinder having an inner and outer surface, said light detection means being secured to said cylinder outer surface.

15. The apparatus of claim 1 wherein said third testing station testing means includes titration means for titrating said third portion of said sample, a housing for holding said third portion, means for causing said third portion to flow in a circular path during said titration and disturbance means located in said circular path for disturbing circular flow of said third portion whereby said titration of said third portion is rendered substantially uniform.

16. The apparatus of claim 15 wherein said housing is circular and has an annular trough formed therein for containing said third portion, said disturbance means positioned in said annular trough for disturbing said circular flow of said third portion.

17. The apparatus of claim 16 wherein said housing is rotatably mounted to a base member, said means for causing said third portion to flow in a circular path including means for rotating said housing.

18. The apparatus of claim 17 wherein said housing includes a removable cover adapted to cover substantially all of said annular trough, said disturbance means being secured to said cover and extending into said annular trough when said cover is mounted over said trough.

19. The apparatus of claim 16 wherein said housing includes a removable cover adapted to cover substantially all of said annular trough, said disturbance means being secured to said cover and extending into said annular trough when said cover is mounted over said trough.

20. The apparatus of claim 18 wherein said disturbance means include a plurality of circularly disposed rods secured at one end to said cover and extending axially perpendicular to said cover into said trough.

21. The apparatus of claim 20 wherein said rods are polytetraflourethylene.

22. The apparatus of claim 19 wherein said disturbance means include a plurality of circularly disposed rods secured at one end to said cover and extending axially perpendicular to said cover into said trough.

23. The apparatus of claim 22 wherein said rods are polytetraflourethylene.

24. The apparatus of claim 18 wherein said titration means include a first and second pair of electrodes, said electrodes being secured to said cover and extending into said annular trough when said cover is mounted over said trough.

25. The apparatus of claim 24 wherein said first pair of electrodes are disposed at a first location in said annular trough and said second pair of electrodes are disposed in said annular trough at a second location substantially diametrically opposite to said first location.

26. The apparatus of claim 16 wherein said titration means include a first and second pair of electrodes extending into said annular trough and in contact with said third portion, said first pair of electrodes being disposed at a first location in said annular trough and said second pair of electrodes being disposed in said annular trough at a second location substantially diametrically opposite to said first location.

27. The apparatus of claim 26 wherein said first pair of electrodes are titration electrodes and said second pair of electrodes are indicator electrodes.

28. The apparatus of claim 15 wherein said third portion is a blood sample, said third sample constituent being chloride, said titration means being operative to coulometrically titrate said third portion employing a silver chloride titration.

29. The apparatus of claim 15 wherein said third testing station includes diluent means for providing a diluent at said testing means before titration for diluting said sample.

30. The apparatus of claim 29 wherein said diluent is a mixture of water, nitric acid, acetic acid and gelatin.

31. The apparatus of claim 27 wherein said third portion is a blood sample, said third sample constituent being chloride, said titration means being operative to coulometrically titrate said third portion employing a silver chloride titration.

32. The apparatus of claim 31 wherein said third testing station includes diluent means for providing a diluent at said testing means before titration for diluting said sample.

33. The apparatus of claim 32 wherein said diluent is a mixture of water, nitric acid, acetic acid and gelatin.

34. The apparatus of claim 32 wherein said second pair of electrodes include a silver chloride reference electrode and a silver chloride electrode and said first pair of electrodes are silver.

35. The apparatus of claim 34 wherein only a predetermined small portion of said silver chloride electrode is placed in said third portion and diluents.

36. The apparatus of claim 27 wherein said second pair of electrodes include an electrode to establish a stable reference voltage and an electrode for developing a signal voltage which varies in accordance with said titration progression.

37. The apparatus of claim 36 wherein said titration electrodes and said indicator electrodes are coupled to circuit means, said circuit means being operative in response to a voltage difference between said indicator electrodes above a first value to couple a signal to said titration electrodes for passage therethrough to titrate said third portion.

38. The apparatus of claim 37 wherein the rate of titration produced by passage of said signal through said titration electrodes is related to the quantity of said third sample constituent, said circuit means including measurement means for measuring the signal coupled to said titration electrodes.

39. The apparatus of claim 38 wherein said measurement means include integration means operative to develop an integration signal in accordance with said signal, said integration signal being proportional to the quantity of said third constituent.

40. The apparatus of claim 37 wherein said circuit means include differential amplifier means coupled to said indicator electrodes and operative to develop a difference voltage which varies in accordance with a difference between said electrodes, comparator means coupled to said differential amplifier means and to a reference potential and operative to develop a first output signal in response to a first difference between said difference signal and said reference signal and a second output signal in response to a second difference between said difference signal and said reference signal, and control means coupled to said comparator and operative in response to said first output signal to couple said signal to said titration electrodes and operative in response to said second output signal to terminate passage of said signal to said titration electrodes.

41. The apparatus of claim 40 wherein said circuit means further include indicator means coupled in series between said control means and said titration electrodes and operative in response to passage of said signal therethrough to provide an indication of passage of signal to said electrodes and for indicating titration.

42. The apparatus of claim 41 wherein said indicator means is a light emitting diode.

43. The apparatus of claim 40 wherein said control means include amplifier means operative in response to said first output signal to develop a constant current and couple same to said electrodes.

44. The apparatus of claim 43 wherein said comparator means include feedback means operative to delay transition from said first to second output signal, said control means being operative in response to said delayed transition to slowly decrease said current coupled to said electrodes.

45. The apparatus of claim 29 wherein said third testing station includes syphon means for syphoning a quantity of said diluent and a third portion from said housing after titration for maintaining a predetermined fluid volume in the said annular trough.

46. The apparatus of claim 1 wherein said second rotating means container allows passage of light through a portion thereof, said second testing means include a photometric analyzing apparatus for analysing said second sample constituent in a known volume of said second portion of sample placed in the said container, said photometric analysis apparatus including, means for alternately supplying light of a first and second wavelength to and through said container along the same path when in said second testing position, means for initiating a chemical process in said second portion in said container for determining said second sample constituent, said means including, a first dye of known concentration added to said container and having an absorption maxima at said first wavelength for absorbing a predetermined amount of said light of first wavelength passing through said container, a second dye of known concentration, at least relative to said first dye, said second dye having an absorption at a second wavelength which varies in accordance with the progression of said chemical process for absorbing an amount of said light of said second wavelength passing through the container in an amount which varies in accordance with progression of said chemical process, detector means for detecting said first and second wavelengths of light passing through said container and for developing first and second detection signals proportional to the intensity of sad detected light wavelengths, comparison means for comparing said alternately received first and second signals, said comparison means developing a first output signal in response to a first difference between said detection signals and a second output signal in response to a second difference, and control means coupled to said comparison means and operative in response to said first output signal to continue said chemical process and operative in response to said second output signal to terminate said chemical process.

47. The apparatus in claim 46 wherein said first dye is methylene blue and said second dye is phenol red, said first dye having a first absorbance at the said first wavelength throughout said chemical process, said second dye having a second absorbance at said second wavelength less than said first absorbance at the start of said chemical reaction and a third absorbance at said second wavelength substantially equal to said first absorbance at the termination of said chemical process.

48. The apparatus of claim 47 wherein said first wavelength is in the red spectrum and said second wavelength is in the green spectrum.

49. The apparatus of claim 48 wherein said second portion is a blood sample, said second sample constituent being bicarbonate, said means for initiating a chemical reaction including titration means operative to coulometrically titrate said second portion.

50. The apparatus of claim 49 wherein said second testing station includes diluent means for providing a diluent in said container for mixture therewith, said diluent including sodium nitrate, nitric acid, water and sodium oxalate.

51. The apparatus of claim 50 wherein said second testing station includes means disposed between said second location and said second testing position and coupled to said containers disposed between second location and said second testing location for coupling air to the mixture in said containers, said air acting to release carbon dioxide from said mixture.

52. The apparatus of claim 51 wherein said means for alternately supplying light include, a light source for providing light, means for directing said light in a path to and through said container at said second testing position and filter means disposed in said path for alternately coupling only said first and second wavelengths of light through said container along said path.

53. The apparatus of claim 51 wherein said detector means include, a photodetector for receiving said light of said first and second wavelength passed through said container at said second testing position said photodetector developing first and second electrical signals in response to said light of first and second wavelengths said first and second electrical signals having a characteristic which varies in accordance with the light intensity producing same, synchronization means synchronized with said filter means and operative to develop first and second signals alternately in synchronism with coupling of said first and second wavelengths to and through said container and to said photodetector, switch means coupled to said synchronization means and operative in response to said first signals to couple said first electrical signals to a first amplifier for developing said first detection signals and operative in response to said second signals to couple the second electrical signals to a second amplifier for developing said second detection signals.

54. The apparatus of claim 53 wherein said chemical process is a titration process, said means for initiating said chemical process including a pair of electrodes inserted in said mixture and coupled to said control means, said control means being operative in response to said first output signal to couple a signal to and through said electrodes for initiating said titration process.

55. The apparatus of claim 54 wherein the signal quantity and period producing said titration is related to the quantity of bicarbonate, said means for initiating a chemical process including measurement means for measuring the signal quantity and period coupled to said titration electrodes.

56. The apparatus of claim 55 wherein said measurement means include integration means operative to develop an integration signal in accordance with said signal, said integration signal being inversely proportional to the quantity of said bicarbonate.

57. The apparatus of claim 46 wherein said means for alternately supplying light include, a light source for providing light, means for directing said light in a path to and through said container at said second testing position and filter means disposed in said path for alternately coupling only said first and second wavelengths of light through said container along said path.

58. The apparatus of claim 46 wherein said detector means include, a photodetector for receiving said light of first and second wavelengths passed through said container at said second testing position, said photodetector developing first and second electrical signals in response to said light of first and second wavelengths, said first and second electrical signals having a characteristic which varies in accordance with the light intensity producing same, synchronization means synchronized with said filter means and operative to develop first and second signals alternately in synchronism with coupling of said first and second wavelengths to and through said container and to said photodetector, switch means coupled to said synchronization means and operative in response to said first signals to couple said first electrical signals to a first amplifier for developing said first detection signal and operative in response to said second signals to couple the second electrical signal to a second amplifier for developing said second detection signal.

59. The apparatus of claim 58 wherein said chemical process is a titration process, said means for initiating said chemical process including a pair of electrodes inserted in said mixture and coupled to said control means, said control means being operative in response to said first output signal to couple a signal to and through said electrodes for initiating said titration process.

60. The apparatus of claim 59 wherein the signal quantity and period producing said titration is related to the quantity of said second sample constituent, said means for initiating a chemical process includes measurement means for measuring the signal quantity and period, coupled to said titration electrodes.

61. The apparatus of claim 60 wherein said measurement means include integration means operative to develop an integration signal in accordance with said signal, said integration means being proportional to the quantity of said second sample constituent.

62. The apparatus of claim 10 wherein said flame photometer means further measures a fourth sample constituent, said first portion is a blood sample, said first sample constituent is sodium, said fourth sample constituent is potassium.

63. The apparatus of claim 62 wherein said first testing station includes diluent means for providing a diluent to said container in said first rotating means for diluting said first portion stored therein and forming a mixture in said container.

64. The apparatus of claim 63 wherein said diluent is a mixture of water, lithium carbonte ($Li_2CO_3$).

65. The apparatus of claim 13 wherein said flame photometer means further measures a fourth sample cofstituent, said first portaof as a bdogd sample, said first saepde cgnstatueft is sodium$ saad fgurt tsaepde cgnstatueft is potassaue.

66. The apparatus of claim 65 wherein said first testing station includes diluent means for providing a diluent to said container in said first rotating means for diluting said first portion stored therein and forming a mixture in said container.

67. The apparatus of claim 66 wherein said diluent is a mixture of water, lithium carbonate ($Li_2CO_3$).

68. The apparatus of claim 67 wherein said lithium, sodium and potassium each burn in said flame and produce light of a particular wavelength, the light intensity of each wavelength being related to concentration of each said constituent, said light detection means responsive to each said light of particular wavelength to develop first, second and third intensity signals respectively, said first being lithium, said second being sodium and said third being potassium, said signals having a characteristic which varies in accordance with said light intensity, said flame photometer including circuit means for analysing said signals for determining said constituents concentration including, integration means coupled to said light detection means for separately integrating said first, second and third signals to develop first, second and third integration signals respectively, comparison means coupled to said integration means and switch means and operative in response to said first integration signal exceeding a predetermined level to actuate said switch means, said switch means being coupled to said integration means and operative to couple said second and third integration signals to indicator means.

* * * * *